(12) United States Patent
Mitrophanous et al.

(10) Patent No.: US 7,419,829 B2
(45) Date of Patent: Sep. 2, 2008

(54) VECTOR SYSTEM

(75) Inventors: Kyri Mitrophanous, Oxford (GB); Jonathan Rohll, Oxford (GB); James Miskin, Oxford (GB); Susan Marie Kingsman, Oxford (GB)

(73) Assignee: Oxford BioMedica (UK) Limited, Oxford (GB)

( * ) Notice: Subject to any disclaimer, the term of this patent is extended or adjusted under 35 U.S.C. 154(b) by 453 days.

(21) Appl. No.: 10/873,573

(22) Filed: Jun. 21, 2004

(65) Prior Publication Data

US 2005/0002907 A1    Jan. 6, 2005

Related U.S. Application Data

(63) Continuation-in-part of application No. 10/408,456, filed on Apr. 7, 2003, now Pat. No. 7,259,015, which is a continuation-in-part of application No. PCT/GB01/04433, filed on Oct. 5, 2001.

(30) Foreign Application Priority Data

Oct. 6, 2000   (GB) ................... 0024550.6

(51) Int. Cl.
| | |
|---|---|
| *C12N 15/63* | (2006.01) |
| *C12N 15/64* | (2006.01) |
| *C12N 15/867* | (2006.01) |
| *C12N 5/10* | (2006.01) |
| *C07H 21/04* | (2006.01) |
| *C07H 21/02* | (2006.01) |
| *A61K 48/00* | (2006.01) |
| *C12Q 1/68* | (2006.01) |
| *C12Q 1/70* | (2006.01) |

(52) U.S. Cl. .................... 435/456; 435/320.1; 435/455; 435/325; 424/93.1; 424/93.2; 424/93.6; 536/23.1; 536/23.72; 536/24.2

(58) Field of Classification Search ........................ None
See application file for complete search history.

(56) References Cited

U.S. PATENT DOCUMENTS

| | | | |
|---|---|---|---|
| 6,103,226 A | 8/2000 | Kang et al. | |
| 6,136,597 A | 10/2000 | Hope et al. | |
| 6,287,814 B1 | 9/2001 | Hope et al. | |
| 6,682,907 B1 * | 1/2004 | Charneau et al. ........... | 435/69.1 |
| 6,969,598 B2 * | 11/2005 | Olsen et al. ................ | 435/69.1 |
| 2003/0044981 A1 * | 3/2003 | Marasco et al. ............ | 435/456 |

FOREIGN PATENT DOCUMENTS

| | | |
|---|---|---|
| WO | WO 93/03143 | 2/1993 |
| WO | WO 94/24870 | 11/1994 |
| WO | WO 97/18319 | 5/1997 |
| WO | WO 98/12338 | 3/1998 |

OTHER PUBLICATIONS

Moffat et al., "L-Dopa and Dopamine-Producing Gene Cassettes for Gene Therapy Approaches to Parkinson's Disease", Experimental Neurology, vol. 11, No. 1, pp. 69-73, Mar. 1, 1997.
Robbins et al., "Viral Vectors for Gene Therapy", Trends in Biotechnology, Elsevier Publications, Cambridge, GB, vol. 16, No. 1, pp. 35-40, 1998.
Hsieh et al., "Improved Gene Expression by a Modified Bicistronic Retroviral Vector", Biochemical and Biophysical Research Communications, vol. 214, pp. 910-917, 1995.
During et al., "In Vivo Expression of Therapeutic Human Genes for Dopamine Production in the Cauditi of MPTP-Treated Monkeys Using an AAV Vector", Gene Therapy, vol. 5, pp. 820-827, 1998.
Metz et al., "Construction and Characterization of Single-Transcript Tricistronic Retroviral Vectors Using Two Internal Ribosome Entry Sites", Somatic Cell and Molecular Genetics, vol. 24, No. 1, pp. 53-69, 1998.
Zheng et al., "Transcripts of Hepatitis B Virus X Gene Derived From Intragenic Promoter", The Journal of Biological Chemistry, vol. 269, No. 36, pp. 22593-22598, 1994.
Flajolet et al., "Woodchuck Hepatitis Virus Enhancer I and Enhancer II are Both Involved in N-*miyc2* Activation in Woodchuck Liver Tumors", Journal of Virology, vol. 72, No. 7, pp. 6175-6180, 1998.
Zufferey, et al., "Woodchuck Hepatitis Virus Posttranscriptional Regulatory Element Enhances Expression ONF Transgenes Delivered by Retroviral Vectors", Journal of Virology, vol. 73, No. 4, pp. 2886-2892, 1999.
K. A. Mitrophanous, et al., Stable Gene Transfer To The Nervous System Using A Non-Primate Lentiviral Vector, Gene Therapy, 1999, vol. 6, p. 1808-1816.
J.C. Olsen, Gene Transfer Vectors Derived From Equine Infectious Anemia Virus, Gene Therapy, 1998, vol. 5, p. 1481-1487.
Nam-Hee Shin, et al., Replication Of Lengthened Moloney Murine Luekemia Virus Genomes Is Impaired At Multiple Stages, Journal of Virology, 2000, vol. 74, No. 6, p. 2694-2702.
Didier Trono, et al., HIV-Based Vectors: Getting The Best Out Of The Worst, The Journal of Gene Medicine, 2000, vol. 2, p. 61-63.

* cited by examiner

*Primary Examiner*—David Guzo
(74) *Attorney, Agent, or Firm*—Frommer Lawrence & Haug LLP; Thomas J. Kowalski; Anne-Marie C. Yvon

(57) ABSTRACT

The present invention provides a vector system comprising a mutated post-transcriptional regulatory element. In particular, the present invention relates to a mutated WPRE sequence that can efficiently express nucleotides of interest in a retroviral vector system. The present invention also relates to methods of delivering and expressing nucleotides of interest to a target cell.

31 Claims, 15 Drawing Sheets

Figure 6

```
WPRE WT     1 AATCAACCTCTGGATTACAAAA-TTTGTGAAAGATTGACTGGTATTCTTA
WPRE SMT    1 AATCAACCTCTGGATTACAAAAATTTGTGAAAGATTGACTGGTATTCTTA
WPRE MUT    1 AATCAACCTCTGGATTACAAAAATTTGTGAAAGATTGACTGGTATTCTTA

WPRE WT    50 ACTATGTTGCTCCTTTTACGCTATGTGGATACGCTGCTTTAATGCCTTTG
WPRE SMT   51 ACTATGTTGCTCCTTTTACGCTATGTGGATACGCTGCTTTAATGCCTTTG
WPRE MUT   51 ACTATGTTGCTCCTTTTACGCTATGTGGATACGCTGCTTTAATGCCTTTG

WPRE WT   100 TATCATGCTATTGCTTCCCGTATGGCTTTCATTTTCTCCTCCTTGTATAA
WPRE SMT  101 TATCATGCTATTGCTTCCCGTATGGCTTTCATTTTCTCCTCCTTGTATAA
WPRE MUT  101 TATCATGCTATTGCTTCCCGTATGGCTTTCATTTTCTCCTCCTTGTATAA

WPRE WT   150 ATCCTGGTTGCTGTCTCTTTATGAGGAGTTGTGGCCCGTTGTCAGGCAAC
WPRE SMT  151 ATCCTGGTTGCTGTCTCTTTATGAGGAGTTGTGGCCCGTTGTCAGGCAAC
WPRE MUT  151 ATCCTGGTTGCTGTCTCTTTATGAGGAGTTGTGGCCCGTTGTCAGGCAAC

WPRE WT   200 GTGGCGTGGTGTGCACTGTGTTTGCTGACGCAACCCCCACTGGTTGGGGC
WPRE SMT  201 GTGGCGTGGTGTGCACTGTGTTTGCTGACGCAACCCCCACTGGTTGGGGC
WPRE MUT  201 GTGGCGTGGTGTGCACTGTGTTTGCTGACGCAACCCCCACTGGTTGGGGC

WPRE WT   250 ATTGCCACCACCTGTCAGCTCCTTTCGGGACTTTCGCTTTCCCCCTCCC
WPRE SMT  251 ATTGCCACCACCTGTCAGCTCCTTTCGGGACTTTCGCTTTCCCCCTCCC
WPRE MUT  251 ATTGCCACCACCTGTCAGCTCCTTTCGGGACTTTCGCTTTCCCCCTCCC

WPRE WT   300 TATTGCCACGGCGGAACTCATCGCCGCCTGCCTTGCCCGCTGCTGGACAG
WPRE SMT  301 TATTGCCACGGCGGAACTCATCGCCGCCTGCCTTGCCCGCTGCTGGACAG
WPRE MUT  301 TATTGCCACGGCGGAACTCATCGCCGCCTGCCTTGCCCGCTGCTGGACAG

WPRE WT   350 GGGCTCGGCTGTTGGGCACTGACAATTCCGTGGTGTTGTCGGGGAAGCTG
WPRE SMT  351 GGGCTCGGCTGTTGGGCACTGACAATTCCGTGGTGTTGTCGGGGAAGCTG
WPRE MUT  351 GGGCTCGGCTGTTGGGCACTGACAATTCCGTGGTGTTGTCGGGGAAGGTC

WPRE WT   400 ACGTCCTTTCCATGGCTGCTCGCCTGTGTTGCCACCTGGATTCTGCGCGG
WPRE SMT  401 ACGTCCTTTCCATGGCTGCTCGCCTGTGTTGCCACCTGGATTCTGCGCGG
WPRE MUT  401 TGCTGAGACTCGGGGCTGCTCGCCTGTGTTGCCACCTGGATTCTGCGCGG

WPRE WT   450 GACGTCCTTCTGCTACGTCCCTTCGGCCCTCAATCCAGCGGACCTTCCTT
WPRE SMT  451 GACGTCCTTCTGCTACGTCCCTTCGGCCCTCAATCCAGCGGACCTTCCTT
WPRE MUT  451 GACGTCCTTCTGCTACGTCCCTTCGGCCCTCAATCCAGCGGACCTTCCTT

WPRE WT   500 CCCGCGGCCTGCTGCCGGCTCTGCGGCCTCTTCCGCGTCTTCGCCTTCGC
WPRE SMT  501 CCCGCGGCCTGCTGCCGGCTCTGCGGCCTCTTCCGCGTCTTCGCCTTCGC
WPRE MUT  501 CCCGCGGCCTGCTGCCGGCTCTGCGGCCTCTTCCGCGTCTTCGCCTTCGC

WPRE WT   550 CCTCAGACGAGTCGGATCTCCCTTTGGGCCGCCTCCCCGCCTG
WPRE SMT  551 CCTCAGACGAGTCGGATCTCCCTTTGGGCCGCCTCCCCGCCTG
WPRE MUT  551 CCTCAGACGAGTCGGATCTCCCTTTGGGCCGCCTCCCCGCCTG
```

Figure 8A

| | | | | | |
|---|---|---|---|---|---|
| tttgagattt | ctgtcgccga | ctaaattcat | gtcgcgcgat | agtggtgttt | atcgccgata | 60 |
| gagatggcga | tattggaaaa | attgatattt | gaaaatatgg | catattgaaa | atgtcgccga | 120 |
| tgtgagtttc | tgtgtaactg | atatcgccat | ttttccaaaa | gtgattttg | ggcatacgcg | 180 |
| atatctggcg | atagcgctta | tatcgtttac | gggggatggc | gatagacgac | tttggtgact | 240 |
| tgggcgattc | tgtgtgtcgc | aaatatcgca | gtttcgatat | aggtgacaga | cgatatgagg | 300 |
| ctatatcgcc | gatagaggcg | acatcaagct | ggcacatggc | caatgcatat | cgatctatac | 360 |
| attgaatcaa | tattggccat | tagccatatt | attcattggt | tatatagcat | aaatcaatat | 420 |
| tggctattgg | ccattgcata | cgttgtatcc | atatcgtaat | atgtacattt | atattggctc | 480 |
| atgtccaaca | ttaccgccat | gttgacattg | attattgact | agttattaat | agtaatcaat | 540 |
| tacggggtca | ttagttcata | gcccatatat | ggagttccgc | gttacataac | ttacggtaaa | 600 |
| tggcccgcct | ggctgaccgc | ccaacgaccc | ccgcccattg | acgtcaataa | tgacgtatgt | 660 |
| tcccatagta | acgccaatag | ggactttcca | ttgacgtcaa | tgggtggagt | atttacggta | 720 |
| aactgcccac | ttggcagtac | atcaagtgta | tcatatgcca | agtccgcccc | ctattgacgt | 780 |
| caatgacggt | aaatggcccg | cctggcatta | tgcccagtac | atgaccttac | gggactttcc | 840 |
| tacttggcag | tacatctacg | tattagtcat | cgctattacc | atggtgatgc | ggttttggca | 900 |
| gtacaccaat | gggcgtggat | agcggtttga | ctcacgggga | tttccaagtc | tccaccccat | 960 |
| tgacgtcaat | gggagtttgt | tttggcacca | aaatcaacgg | gactttccaa | aatgtcgtaa | 1020 |
| caactgcgat | cgcccgcccc | gttgacgcaa | atgggcggta | ggcgtgtacg | gtgggaggtc | 1080 |
| tatataagca | gagctcgttt | agtgaaccgg | gcactcagat | tctgcggtct | gagtcccttc | 1140 |
| tctgctgggc | tgaaaaggcc | tttgtaataa | atataattct | ctactcagtc | cctgtctcta | 1200 |
| gtttgtctgt | tcgagatcct | acagttggcg | cccgaacagg | gacctgagag | gggcgcagac | 1260 |
| cctacctgtt | gaacctggct | gatcgtagga | tccccgggac | agcagaggag | aacttacaga | 1320 |
| agtcttctgg | aggtgttcct | ggccagaaca | caggaggaca | ggtaagattg | ggagaccctt | 1380 |
| tgacattgga | gcaaggcgct | caagaagtta | gagaaggtga | cggtacaagg | gtctcagaaa | 1440 |
| ttaactactg | gtaactgtaa | ttgggcgcta | agtctagtag | acttatttca | ttgataccaa | 1500 |
| ctttgtaaaa | gaaaaggact | ggcagctgag | ggattgtcat | tccattgctg | gaagattgta | 1560 |
| actcagacgc | tgtcaggaca | agaaagagag | gcctttgaaa | gaacattggt | gggcaatttc | 1620 |

Figure 8B

```
tgctgtaaag attgggcctc cagattaata attgtagtag attggaaagg catcattcca   1680
gctcctaaga gcgaaatatt gaaaagaaga ctgctaataa aaagcagtct gagccctctg   1740
aagaatatct ctagaactag tggatccccc gggccaaaac ctagcgccac catgattgaa   1800
caagatggat tgcacgcagg ttctccggcc gcttgggtgg agaggctatt cggctatgac   1860
tgggcacaac agacaatcgg ctgctctgat gccgccgtgt tccggctgtc agcgcagggg   1920
cgcccggttc tttttgtcaa gaccgacctg tccggtgccc tgaatgaact gcaggacgag   1980
gcagcgcggc tatcgtggct ggccacgacg ggcgttcctt gcgcagctgt gctcgacgtt   2040
gtcactgaag cgggaaggga ctggctgcta ttgggcgaag tgccggggca ggatctcctg   2100
tcatctcacc ttgctcctgc cgagaaagta tccatcatgg ctgatgcaat gcggcggctg   2160
catacgcttg atccggctac ctgcccattc gaccaccaag cgaaacatcg catcgagcga   2220
gcacgtactc ggatggaagc cggtcttgtc gatcaggatg atctggacga agagcatcag   2280
gggctcgcgc cagccgaact gttcgccagg ctcaaggcgc gcatgcccga cggcgaggat   2340
ctcgtcgtga cccatggcga tgcctgcttg ccgaatatca tggtggaaaa tggccgcttt   2400
tctggattca tcgactgtgg ccggctgggt gtggcggacc gctatcagga catagcgttg   2460
gctacccgtg atattgctga agagcttggc ggcgaatggg ctgaccgctt cctcgtgctt   2520
tacggtatcg ccgctcccga ttcgcagcgc atcgccttct atcgccttct tgacgagttc   2580
ttctgagcgg ccgcgaattc aaaagctaga gtcgactcta gggagtgggg aggcacgatg   2640
gccgctttgg tcgaggcgga tccggccatt agccatatta ttcattggtt atatagcata   2700
aatcaatatt ggctattggc cattgcatac gttgtatcca tatcataata tgtacattta   2760
tattggctca tgtccaacat taccgccatg ttgacattga ttattgacta gttattaata   2820
gtaatcaatt acggggtcat tagttcatag cccatatatg gagttccgcg ttacataact   2880
tacggtaaat ggcccgcctg gctgaccgcc caacgacccc cgcccattga cgtcaataat   2940
gacgtatgtt cccatagtaa cgccaatagg gactttccat tgacgtcaat gggtggagta   3000
tttacggtaa actgcccact tggcagtaca tcaagtgtat catatgccaa gtacgccccc   3060
tattgacgtc aatgacggta aatggcccgc ctggcattat gcccagtaca tgaccttatg   3120
ggactttcct acttggcagt acatctacgt attagtcatc gctattacca tggtgatgcg   3180
gttttggcag tacatcaatg ggcgtggata gcggtttgac tcacggggat ttccaagtct   3240
```

Figure 8C

```
ccaccccatt gacgtcaatg ggagtttgtt ttggcaccaa aatcaacggg actttccaaa      3300
atgtcgtaac aactccgccc cattgacgca aatgggcggt aggcatgtac ggtgggaggt      3360
ctatataagc agagctcgtt tagtgaaccg tcagatcgcc tggagacgcc atccacgctg      3420
ttttgacctc catagaagac accgggaccg atccagcctc cgcggcccca agctagtcga      3480
ctttaagctt ctcgagaatt cgtgcaccat ggtgaaggta ccctggttcc aagaaaagt       3540 gtcagagctg gacaagtgtc atcacctggt caccaagttc gacccgacc tggacttgga       3600 ccaccccggc ttctcggacc aggtgtaccg ccagcgcagg aagctgatcg ctgagatcgc      3660
cttccagtac aggcacggcg acccgatccc ccgtgtggag taccgccg aggagatcgc       3720 cacctggaag gaggtctaca ccaccctgaa gggcctctac gccacccacg cctgcgggga      3780
gcacctggag gcctttgctt tgctggagcg cttcagcggc taccgggaag acaacatccc      3840
ccagctggag gacgtctccc gcttcctgaa ggagcgcaca ggcttccagc tgcggcccgt      3900
ggccggcctg ctgtccgccc gggacttcct ggccagcctg ccttccgcg tgttccagtg      3960 cacccagtat atccgccacg cgtcctcgcc catgcactcc cctgagccgg actgctgcca      4020
cgagctgctg ggcacgtgc ccatgctggc cgaccgcacc ttcgcgcagt tcagccagga      4080
catcggcctg gcgtccctgg gggccagcga tgaggaaatc gagaagctgt ccactctgta      4140
ctggttcacg gtggagttcg ggctgtgtaa gcagaacggg gaggtgaagg cctatggtgc      4200
cgggctgctg tcctcctacg gggagctcct gcactgcctg tctgaggagc ctgagatccg      4260
ggccttcgac cctgaggctg cggccgtgca gccctaccaa gaccagacgt accagtcagt      4320
ctacttcgtg tctgagagct cagcgacgc caaggacaag ctcaggagct atgccagccg       4380
catccagcgc cccttctccg tgaagttcga cccgtacacc ctggccatcg acgtgctgga      4440
cagcccccag gccgtgcggc gctccctgga gggtgtccag gatgagctgg acacccttgc      4500
ccatgcgctg agcgccatcg gctgagcagt ggcggccgca ctagaggaat tcgccctct      4560 ccctcccccc ccctaacgt tactggccga agccgcttgg aataaggccg gtgtgtgttt      4620
gtctatatgt gattttccac catattgccg tcttttggca atgtgagggc ccggaaacct      4680
ggccctgtct tcttgacgag cattcctagg ggtctttccc ctctcgccaa aggaatgcaa      4740
ggtctgttga atgtcgtgaa ggaagcagtt cctctggaag cttcttgaag acaaacaacg      4800
tctgtagcga ccctttgcag gcagcggaac cccccacctg gcgacaggtg cctctgcggc      4860
```

Figure 8D

```
caaaagccac gtgtataaga tacacctgca aaggcggcac aaccccagtg ccacgttgtg    4920
agttggatag ttgtggaaag agtcaaatgg ctctcctcaa gcgtagtcaa caagggctg     4980
aaggatgccc agaaggtacc ccattgtatg ggaatctgat ctggggcctc ggtgcacatg    5040
ctttacatgt gtttagtcga ggttaaaaaa gctctaggcc ccccgaacca cggggacgtg    5100
gttttccttt gaaaaacacg atgataccat ggacgccagt gagttccgaa ggcgcggcaa    5160
ggagatggtg gactacgtgg ccaactacat ggaaggcatc gagggccgcc aagtctaccc    5220
cgacgtggag cccggctacc tgcgcccgct gatccccgcc gctgcccctc aggagcccga    5280
caccttcgag gacatcatca cgacgtgga gaagatcatc atgcctggcg tgacgcactg     5340
gcacagcccc tacttcttcg cctacttccc caccgccagc tcgtacccgg ccatgctggc    5400
ggacatgctg tgcggggcca ttggctgcat cggcttctcc tgggcggcga gcccagcgtg    5460
caccgagctg gagaccgtga tgatggactg gctcgggaag atgctggagc tcccaaaggc    5520
gttcttgaac gagaaggctg gcgaggggg cggcgtgatc cagggcagcg ccagcgaggc     5580
caccctggtg gccctgctgg ccgctcggac caaagtgatc caccggctgc aggcagcgtc    5640
cccagagctc acccaggccg ctatcatgga gaagctggtg cttactcct ccgatcaggc     5700
acactcctcc gtggaacgcg ctgggctcat tggtggagtg aagctcaagg ccatccccag    5760
cgatggcaac ttcgccatgc gtgcgagcgc cctgcaggaa gccctggaga gagacaaggc    5820
ggctggcctg attcctttct tcatggtggc caccctgggg accacaacat gctgctcctt    5880
cgacaacctc ctcgaagtcg gtcctatctg caacaaggaa gacatctggc tgcacgttga    5940
tgcagcctac gcaggcagcg cattcatctg ccctgagttc cggcaccttc tgaacggagt    6000
ggagttcgca gatagcttca acttcaatcc ccacaagtgg ctattggtga atttcgactg    6060
cagcgccatg tgggtgaaga agcgcaccga cctcacggga gccttccgcc tggaccccac    6120
ttacctgaag cacagccacc aggattcagg gcttatcact gactaccggc actggcagat    6180
cccactgggc cgcagattcc gcagcttgaa gatgtggttc gtattcagga tgtatggagt    6240
caagggactg caggcttata tccgcaagca tgtccagctg tcccatgagt ttgagtcact    6300
ggtgcgccag gatccccgct ttgaaatctg tgtggaagtc attctggggc ttgtctgctt    6360
tcggctaaag ggttccaaca aagtgaatga agctcttctg caaaggatca acagtgccaa    6420
aaaaatccac ttggttccat gtcacctcag ggacaagttt gtcctgcgct ttgccatctg    6480
```

Figure 8E

```
ttctcgcacc gtggaatctg cccatgtgca gcgggcctgg gaacacatca aagagctggc    6540
ggccgacgtg ctgcgagcag agagggagta gctcgaaaac ccgctgatca gcctcgactg    6600
tgccttctag ttgccagcca tctgttgttt gcccctcccc cgtgccttcc ttgagaattc    6660
ctcgacgtag atatcttaaa acagctctgg ggttgtaccc accccagagg cccacgtggc    6720
ggctagtact ccggtattgc ggtacctttg tacgcctgtt ttatactccc ttcccccgta    6780
acttagaagc acaatgtcca agttcaatag gaggggtac aaaccagtac caccacgaac    6840
aagcacttct gttccccgg tgaggctgta taggctgttt ccacggctaa agcggctga    6900
tccgttatcc gctcatgtac ttcgagaagc ctagtatcac cttggaatct tcgatgcgtt    6960
gcgctcaaca ctcaaccca gagtgtagct taggtcgatg agtctggacg ttcctcaccg    7020
gcgacggtgg tccaggctgc gttggcggcc tacctgtggc ccaaagccac aggacgctag    7080
ttgtgaacaa ggtgtgaaga gcctattgag ctacctgaga gtcctccggc ccctgaatgc    7140
ggctaatcct aaccacggag caggcagtgg caatccagcg accagcctgt cgtaacgcgc    7200
aagttcgtgg cggaaccgac tactttgggt gtccgtgttt ccttttattt ttacaatggc    7260
tgcttatggt gacaatcatt gattgttatc ataaagcaaa ttggattggc catccggtga    7320
gaatttgatt attaaattac tctcttgttg ggattgctcc tttgaaatct tgtgcactca    7380
cacctattgg aattacctca ttgttaaacg cgtctagcta gcgccaccat ggagaagggc    7440
cctgtgcgcg ccccggccga aagccgcgc ggcgcccgct gcagcaatgg gttccccgag    7500
cgcgacccgc cgcgccccgg gcccagcagg ccggccgaga agccccgcg ccccgaggcc    7560
aagagcgcgc agcccgcgga cggctggaag ggcgagcgcc cccgcagcga ggaggacaac    7620
gagctgaacc tccctaacct ggccgccgcc tactcctcca tcctgagctc gctgggcgag    7680
aaccccagc ggcagggct gctcaagacc ccctggaggg cggcctcggc catgcagttc    7740
ttcaccaagg gctaccagga gaccatctca gacgtcctga acgacgctat cttcgacgaa    7800
gatcacgatg agatggtgat cgtgaaggac atagacatgt tctccatgtg cgagcaccac    7860
ctggtgccat ttgtgggaaa ggtccatatc ggctacctgc taacaagca ggtcctgggc    7920
ctcagcaagc tggcgaggat tgtggaaatc tatagtagaa gactacaggt tcaggagcgc    7980
cttaccaaac aaattgctgt ggcaatcacg gaagccttgc ggcctgctgg agtcggggtc    8040
gtggtggaag caacacacat gtgtatggtg atgcgaggtg tacagaaaat gaacagcaaa    8100
```

Figure 8F

```
accgtgacca gcacaatgct gggtgtgttc cgggaggatc caaagactcg ggaagagttc    8160
ctgactctca tcaggagctg aagaattcct cgacagctta tcgataatca acctctggat    8220
tacaaaattt gtgaaagatt gactggtatt cttaactatg ttgctccttt tacgctatgt    8280
ggatacgctg ctttaatgcc tttgtatcat gctattgctt cccgtatggc tttcattttc    8340
tcctccttgt ataaatcctg gttgctgtct ctttatgagg agttgtggcc cgttgtcagg    8400
caacgtggcg tggtgtgcac tgtgtttgct gacgcaaccc ccactggttg gggcattgcc    8460
accacctgtc agctcctttc cgggactttc gctttccccc tccctattgc cacggcggaa    8520
ctcatcgccg cctgccttgc ccgctgctgg acaggggctc ggctgttggg cactgacaat    8580
tccgtggtgt tgtcggggaa atcatcgtcc tttccttggc tgctcgcctg tgttgccacc    8640
tggattctgc gcgggacgtc cttctgctac gtcccttcgg ccctcaatcc agcggacctt    8700
ccttcccgcg gcctgctgcc ggctctgcgg cctcttccgc gtcttcgcct tcgccctcag    8760
acgagtcgga tctccctttg ggccgcctcc ccgcatcgat accgtcgaat tggaagagct    8820
ttaaatcctg gcacatctca tgtatcaatg cctcagtatg tttagaaaaa caaggggga    8880
actgtggggt ttttatgagg ggttttatac aattgggcac tcagattctg cggtctgagt    8940
cccttctctg ctgggctgaa aaggcctttg taataaatat aattctctac tcagtccctg    9000
tctctagttt gtctgttcga gatcctacag agctcatgcc ttggcgtaat catggtcata    9060
gctgtttcct gtgtgaaatt gttatccgct cacaattcca cacaacatac gagccgggag    9120
cataaagtgt aaagcctggg gtgcctaatg agtgagctaa ctcacattaa ttgcgttgcg    9180
ctcactgccc gctttccagt cgggaaacct gtcgtgccag ctgcattaat gaatcggcca    9240
acgcgcgggg agaggcggtt tgcgtattgg gcgctcttcc gcttcctcgc tcactgactc    9300
gctgcgctcg gtcgttcggc tgcggcgagc ggtatcagct cactcaaagg cggtaatacg    9360
gttatccaca gaatcagggg ataacgcagg aaagaacatg tgagcaaaag gccagcaaaa    9420
ggccaggaac cgtaaaaagg ccgcgttgct ggcgtttttc cataggctcc gcccccctga    9480
cgagcatcac aaaaatcgac gctcaagtca gaggtggcga acccgacag gactataaag    9540
ataccaggcg tttccccctg gaagctccct cgtgcgctct cctgttccga ccctgccgct    9600
taccggatac ctgtccgcct ttctcccttc gggaagcgtg gcgctttctc atagctcacg    9660
ctgtaggtat ctcagttcgg tgtaggtcgt tcgctccaag ctgggctgtg tgcacgaacc    9720
```

Figure 8G

```
ccccgttcag cccgaccgct gcgccttatc cggtaactat cgtcttgagt ccaacccggt    9780
aagacacgac ttatcgccac tggcagcagc cactggtaac aggattagca gagcgaggta    9840
tgtaggcggt gctacagagt tcttgaagtg gtggcctaac tacggctaca ctagaaggac    9900
agtatttggt atctgcgctc tgctgaagcc agttaccttc ggaaaaagag ttggtagctc    9960
ttgatccggc aaacaaacca ccgctggtag cggtggtttt tttgtttgca agcagcagat   10020
tacgcgcaga aaaaaggat ctcaagaaga tcctttgatc ttttctacgg ggtctgacgc    10080
tcagtggaac gaaaactcac gttaagggat tttggtcatg agattatcaa aaggatctt    10140
cacctagatc cttttaaatt aaaaatgaag ttttaaatca atctaaagta tatatgagta   10200
aacttggtct gacagttacc aatgcttaat cagtgaggca cctatctcag cgatctgtct   10260
atttcgttca tccatagttg cctgactccc cgtcgtgtag ataactacga tacgggaggg   10320
cttaccatct ggccccagtg ctgcaatgat accgcgagac ccacgctcac cggctccaga   10380
tttatcagca ataaaccagc cagccggaag ggccgagcgc agaagtggtc ctgcaacttt   10440
atccgcctcc atccagtcta ttaattgttg ccgggaagct agagtaagta gttcgccagt   10500
taatagtttg cgcaacgttg ttgccattgc tacaggcatc gtggtgtcac gctcgtcgtt   10560
tggtatggct tcattcagct ccggttccca acgatcaagg cgagttacat gatcccccat   10620
gttgtgcaaa aaagcggtta gctccttcgg tcctccgatc gttgtcagaa gtaagttggc   10680
cgcagtgtta tcactcatgg ttatggcagc actgcataat tctcttactg tcatgccatc   10740
cgtaagatgc ttttctgtga ctggtgagta ctcaaccaag tcattctgag aatagtgtat   10800
gcggcgaccg agttgctctt gcccggcgtc aatacgggat aataccgcgc cacatagcag   10860
aactttaaaa gtgctcatca ttggaaaacg ttcttcgggg cgaaaactct caaggatctt   10920
accgctgttg agatccagtt cgatgtaacc cactcgtgca cccaactgat cttcagcatc   10980
ttttactttc accagcgttt ctgggtgagc aaaaacagga aggcaaaatg ccgcaaaaaa   11040
gggaataagg gcgacacgga aatgttgaat actcatactc ttcctttttc aatattattg   11100
aagcatttat cagggttatt gtctcatgag cggatacata tttgaatgta tttagaaaaa   11160
taaacaaata ggggttccgc gcacatttcc ccgaaaagtg ccacctaaat tgtaagcgtt   11220
aatattttgt taaaattcgc gttaaatttt tgttaaatca gctcatttttt aaccaatag   11280
gccgaaatcg gcaaaatccc ttataaatca aagaataga ccgagatagg gttgagtgtt   11340
```

Figure 8H

```
gttccagttt ggaacaagag tccactatta aagaacgtgg actccaacgt caaagggcga   11400
aaaaccgtct atcagggcga tggcccacta cgtgaaccat caccctaatc aagttttttg   11460
gggtcgaggt gccgtaaagc actaaatcgg aaccctaaag ggagcccccg atttagagct   11520
tgacggggaa agccaacctg gcttatcgaa attaatacga ctcactatag ggagaccggc   11580
agatcttgaa taataaaatg tgtgtttgtc cgaaatacgc gt                      11622
```

VECTOR SYSTEM

CROSS-REFERENCE TO RELATED APPLICATIONS

This application is a continuation-in-part of U.S. application Ser. No. 10/408,456, filed on Apr. 7, 2003, now U.S. Pat. No. 7,259,015 which is a continuation-in-part of International Application No. PCT/GB01/04433, filed on Oct. 5, 2001, which claims priority to British Application No. GB 0024550.6, filed on Oct. 6, 2000.

This application makes reference to U.S. application Ser. No. 10/008,610, filed on Nov. 8, 2001, which claims priority to U.S. Provisional Application Ser. No. 60/247,604, filed on Nov. 9, 2000.

This application also makes reference to U.S. application Ser. No. 10/841,603, filed on May 7, 2004, which is a continuation-in-part of International application No. PCT/GB03/064665, filed on Feb. 3, 2003, which claims priority to British application Nos. GB 0202403.2, filed on Feb. 1, 2002, and GB 0212768.6, filed on May 31, 2002.

This application also makes reference to U.S. Pat. Nos. 6,312,682 and 6,312,683, the contents of which are expressly incorporated herein by reference.

All of the foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates to a vector system comprising a mutated post-transcriptional regulatory element. In particular, the present invention relates to a mutated WPRE sequence that can efficiently express nucleotides of interest in a retroviral vector system. The present invention also relates to methods of delivering and expressing nucleotides of interest to a target cells.

BACKGROUND OF THE INVENTION

Retroviral vector systems, such as lentiviral vector systems, have been proposed as a delivery system for, inter alia, the transfer of a nucleotide of interest to one or more sites of interest. Indeed, the concept of using viral vectors for gene therapy is well known (Verma and Somia (1997) Nature 389: 239-242). Retrovirus genomes contain accessory genes, such as a rev gene, a tat gene, a vif gene, a nef gene, a vpr gene or an S2 gene. The deletion of such accessory genes, particularly when using retroviral vector systems in gene therapy, is highly advantageous. Firstly, it permits vectors to be produced without genes normally associated with disease in retroviral (e.g. HIV) infections. Secondly, the deletion of accessory genes permits the vector to package more heterologous DNA. Thirdly, genes whose function is unknown such as dUTPase and S2, may be omitted, thus reducing the risk of causing undesirable effects.

We have previously taught, e.g. in WO98/17815, how to remove many of the accessory genes. Further, in WO99/45126, we describe codon optimisation of the gag-pol sequence as a means of seeking to overcome the Rev/RRE requirement for export and to enhance RNA stability. However, the need remains to provide strategies for the provision of useful and safe viral vectors, and efficient means for their production.

WO 98/18934 involves gene transfer systems, such as retroviral vectors; and there are other documents that may involve retroviral vectors (See, e.g., Naldini et al., 1996 Science 272, 263; PCT/GB96/01230; Bowtell et al., 1988 J. Virol. 62, 2464; Correll et al., 1994 Blood 84, 1812; Emerman and Temin 1984 Cell 39, 459; Ghattas et al., 1991 Mol. Cell. Biol. 11, 5848; Hantzopoulos et al., 1989 PNAS 86, 3519; Hatzoglou et al., 1991 J. Biol. Chem 266, 8416; Hatzoglou et al., 1988 J. Biol. Chem 263, 17798; Li et al., 1992 Hum. Gen. Ther. 3, 381; McLachlin et al., 1993 Virol. 195, 1; Overell et al., 1988 Mol. Cell Biol. 8, 1803; Scharfman et al., 1991 PNAS 88, 4626; Vile et al., 1994 Gene Ther 1, 307; Xu et al., 1989 Virol. 171, 331; Yee et al., 1987 PNAS 84, 5197; WO99/15683; Verma and Somia (1997) Nature 389:239-242; page 446, Chapter 9 of Coffin et al "Retroviruses" 1997 Cold Spring Harbour Laboratory Press).

Post-Transcriptional Regulatory Elements

One shortcoming of retroviral vectors, whether based on retroviruses or lentiviruses, is their frequent inability to generate high levels of gene expression, particularly in vivo. Many steps, both transcriptional and post-transcriptional, are involved in regulating gene expression. Therefore, it is possible to enhance expression of transgenes delivered by retroviral vectors through the addition of elements known to post-transcriptionally increase gene expression. The best-known example is the inclusion of introns within the expression cassette (Choi, T. et al, (1991) Mol. Cell. Biol. 9: 3070-3074). Many gene transfer experiments, performed both in vitro and in vivo, have demonstrated that the presence of an intron can facilitate gene expression.

Other types of elements can also be used to stimulate heterologous gene expression post-transcriptionally. These elements, unlike introns, are advantageous in that they do not require splicing events. For instance, previous studies have suggested that the hepatitis B virus (HBV) post-transcriptional regulatory element (PRE) and an intron are functionally equivalent (Huang, Z. M. and Yen, T. S. (1995) Mol. Cell. Biol. 15: 3864-3869). Woodchuck hepatitis virus (WHV), a close relative of HBV, also harbors a PRE (hereinafter referred to as WPRE; see U.S. Pat. Nos. 6,136,597 and 6,287,814). The WPRE has been shown to be significantly more active than its HBV counterpart, correlating to the presence of additional cis-acting sequences not found in the HBV PRE. Insertion of the WPRE in lentiviral vectors resulted in significant stimulation of expression of reporter genes such as luciferase and green fluorescent protein (GFP) in a variety of cells spanning different species (Zufferey, R. et al, (1999) J. Virol 73: 2886-2892). Stimulation was irrespective of the cycling status of transduced cells.

The WPRE contains three cis-acting sequences important for its function in enhancing expression levels. However, in addition, it contains a fragment of approximately 180 base pairs (bp), comprising the 5' end of the WHV X protein open reading frame, together with its associated promoter. The full-length X protein has been implicated in tumorigenesis (Flajolet, M. et al, (1998) J. Virol. 72: 6175-6180). Cis-activation of myc family oncogenes due to the insertion of viral DNA into the host genome is known to be a key mechanism of WHV-mediated carcinogenesis (Buendia, M. A. (1994) In C. Bréchot (ed.), Primary liver cancer: etiological and progression factors, p. 211-224; CRC Press, Boca Raton, Fla.; Fourel, G. (1994) In F. Tronche and M. Yaniv (ed.), Liver gene expression, p. 297-343; R. G. Landes Company, Austin, Tex.).

The present inventors have now shown that mutation of a region of the WPRE corresponding to the X protein ORF ablates the tumorigenic activity of the X protein, thereby allowing the WPRE to be used safely in retroviral and lentiviral expression vectors to enhance expression levels of heterologous genes or nucleotides of interest. Moreover, the modified WPRE can be used to identify genes involved in tumorigenesis by identifying its integration site in the chromosomal DNA of cells of interest.

SUMMARY OF THE INVENTION

According to a first aspect of the present invention, there is provided an isolated nucleic acid molecule comprising a woodchuck post-transcriptional regulatory element (WPRE) containing an X region, wherein the WPRE has a mutation in the X region, whereby expression of a functional X protein is prevented. In a preferred embodiment, the isolated nucleic acid molecule comprises the sequence of SEQ ID NO:1.

In a preferred embodiment, the X region comprises a sufficient number of base pair changes such that reversion to the wild type WPRE sequence is substantially prevented. In particularly preferred embodiments, the X region sequence comprises at least six, seven, eight, nine, ten, eleven, twelve or thirteen base pair changes, relative to the wild type WPRE sequence. Preferably, the X region of the invention comprises the sequence:

```
       5        10        15
     GTCTGCTGAGAGACTCGG        (SEQ ID NO:2)
```

Preferably, the X region comprises a promoter sequence and the mutation is partly or entirely in the promoter sequence. Preferably, the wild type WPRE X region promoter sequence comprises the sequence:

```
       5        10        15        20
     GGGGAAGCTGACGTCCTTTCC        (SEQ ID NO:3)
```

Preferably, the X region promoter sequence comprises at least six, seven, eight, nine, ten or eleven base pair changes relative to the wild type WPRE sequence. Even more preferably, the X region promoter sequence has a mutation at one or more of positions 12, 13, 15, 16, 17, 18, 19 and/or 20 of the wild type sequence. Advantageously, the X region promoter sequence of the invention is:

```
       5        10        15        20
     GGGAAGGTCTGCTGAGACTC        (SEQ ID NO:4)
```

Alternatively, or in addition, the X region comprises an initiation codon and the mutation is partly or entirely in the initiation codon. Preferably, the initiation codon of the wild type WPRE is A at position 1, T at position 2 and G at position 3. In one embodiment, the initiation codon comprises a nucleotide other than T at position 2. In another embodiment, the mutation comprises at least two base pair changes relative to the wild type WPRE sequence. Preferably, the X region initiation codon is GGG.

Preferably, the X protein is not expressed or is non-functional.

In a second aspect of the present invention, a retroviral vector genome comprising at least one NOI and the isolated nucleic acid molecule according to the first aspect of the invention is provided.

Preferably, the retroviral vector genome is a lentiviral vector genome. Particularly, the lentiviral vector genome can be a minimal lentiviral vector genome. The lentiviral vector genome can be derived from a viral species selected from the group consisting of human immunodeficiency virus (HIV), simian immunodeficiency virus (SIV), visna/maedi virus (VMV), caprine arthritis-encephalitis virus (CAEV), equine infectious anaemia virus (EIAV), feline immunodeficiency virus (FIV), and bovine immunodeficiency virus (BIV). Preferably, the lentiviral vector genome is derived from a non-primate lentivirus.

In another preferred embodiment, a nucleic acid sequence encoding Rev, or a functional equivalent thereof, is disrupted such that the nucleic acid sequence is incapable of encoding the functional Rev or is removed from the vector genome.

In yet another preferred embodiment, a nucleic acid sequence encoding Tat is disrupted such that the nucleic acid sequence is incapable of encoding functional Tat or is removed from the vector genome.

A preferred embodiment of the present invention provides a retroviral vector genome that comprises a central polypurine tract (cPPT) sequence. In another preferred embodiment, the retroviral vector genome comprises a gag-packaging signal having ATG motifs, and wherein the ATG motifs are ATTG motifs.

In another preferred embodiment, the retroviral vector genome is multicistronic and can comprise at least one internal regulatory element. Preferably, the internal regulatory element is a promoter or an internal ribosomal entry site (IRES).

According to a third aspect of the present invention, there is provided a retroviral vector system for producing a retrovirus-derived vector particle, comprising (i) the retroviral vector genome according to the second aspect of the invention, (ii) a nucleotide sequence encoding retroviral gag and pol proteins; (iii) nucleotide sequences encoding other essential viral packaging components not encoded by the nucleotide sequence of (ii). Preferably, nucleic acid sequence(s) encoding at least one of Vpr, Vif, Tat, Nef, or analogous auxiliary genes, from the retrovirus from which the particles are derived, are disrupted such as said nucleic acid sequence(s) are incapable of encoding functional Vpr, Vif, Tat, Nef, or analogous auxiliary proteins, or are removed from the system.

Preferably, the vector system is pseudotyped with at least part of a heterologous env protein. In particular, the heterologous env protein is derivable from Rabies-G or VSV-G.

In a fifth aspect of the invention, a viral particle produced from the retroviral vector system of the present invention is provided.

A sixth aspect of the invention provides a cell that has been transduced with the retroviral vector system of the present invention.

In a seventh aspect of the invention, a composition comprising the retroviral vector genome of the present invention, together with a carrier or a diluent, is provided.

An eighth aspect of the invention provides a composition comprising a viral particle of the present invention, together with a carrier or a diluent.

A ninth aspect of the invention provides a method of delivering at least one NOI to a target cells, comprising introducing the retroviral vector genome of the present invention into the target cell, whereby the NOI is delivered to the target cell.

According to a tenth aspect, there is provided a method of identifying genes involved in tumorigenesis, comprising the steps of introducing the isolated nucleic acid molecule of the present invention into a cell of interest, whereby the nucleic acid is recombined into chromosomal DNA of the cell of interest; determining whether the cell of interest forms a tumor; and, if the cell of interest forms a tumor, locating a site of recombination in the chromosomal DNA, and identifying a gene near or adjacent to the site of recombination; thereby identifying the gene involved in tumorigenesis.

The present invention will now be described only by way of example, in which reference will be made to the following Figures.

BRIEF DESCRIPTION OF THE DRAWINGS

FIG. 6 shows a comparison of the nucleotide sequence of wild-type WPRE sequence from WHV8 (WT) (SEQ ID NO:5), WPRE from SMART2 vectors (SMT) (SEQ ID NO:6), and WPRE incorporating nucleotide changes designed to prevent transcription from the X promoter and translation from the X protein initiation codon (MUT) (SEQ ID NO:1). The region containing the X promoter and the X protein initiation codon is underlined. Differences between the WPRE nucleotide sequences are shown in bold type.

FIGS. 8A-8H show the sequence of pONY8.9.4 MV optiY (SEQ ID NO:7).

DETAILED DESCRIPTION OF THE INVENTION

Figure 1:
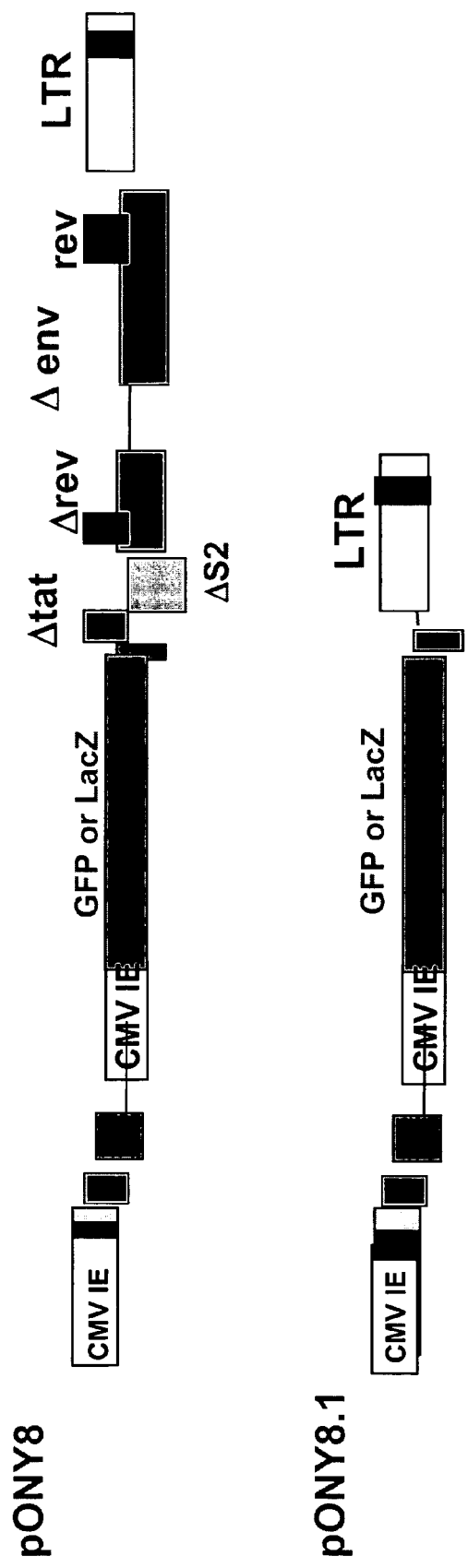
FIG. 1 shows a schematic diagram of EIAV minimal vectors.
Figure 2:
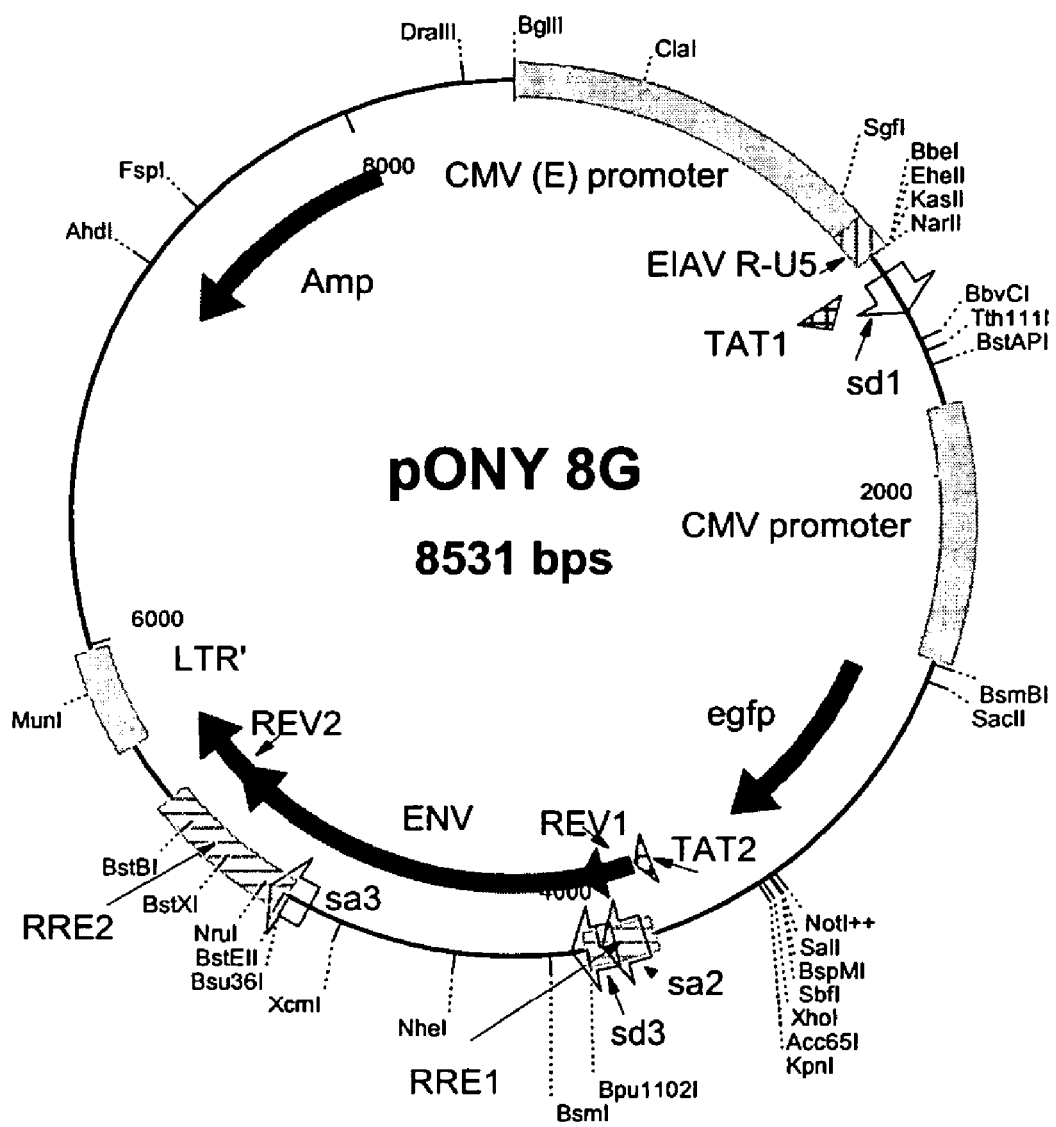
FIG. 2 shows a plasmid map of pONY8G
Figure 3:
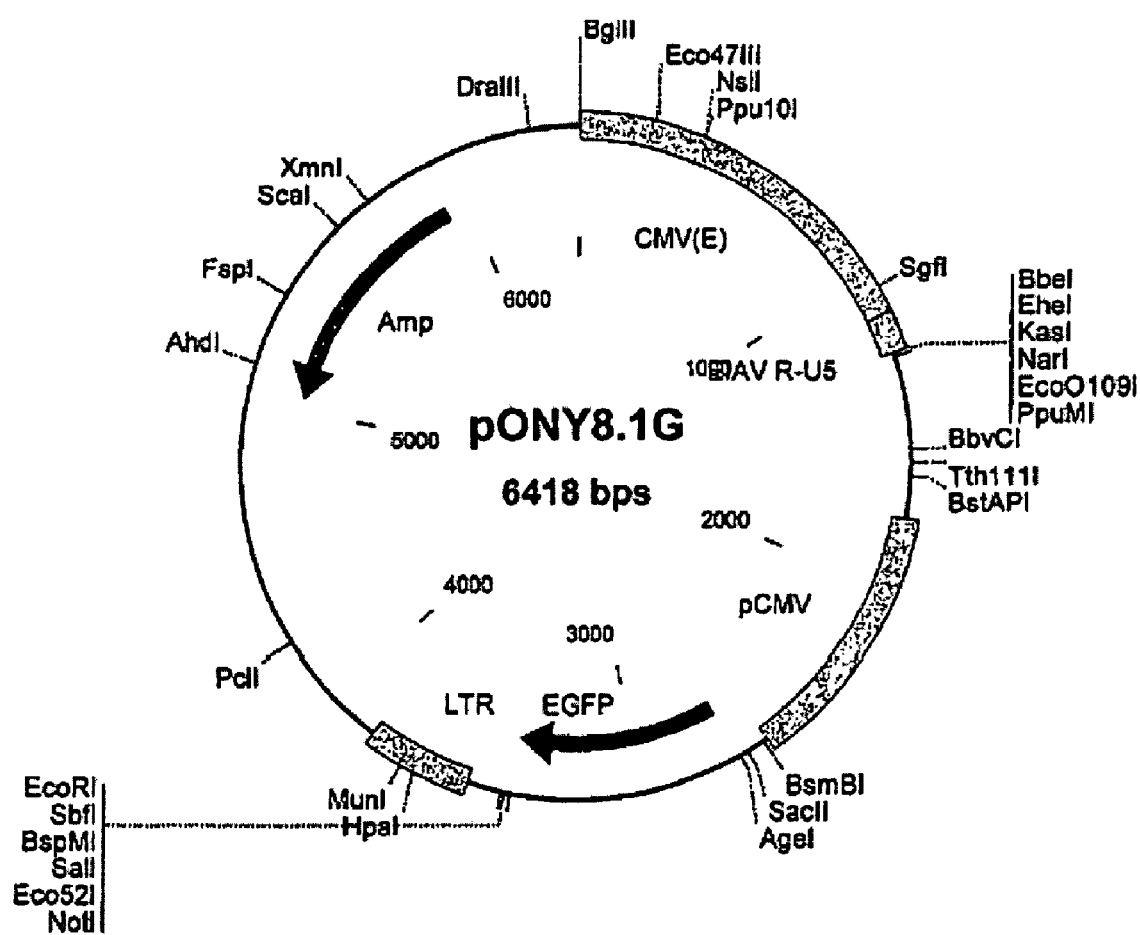
FIG. 3 shows a plasmid map of pONY8.1G
Figure 4:
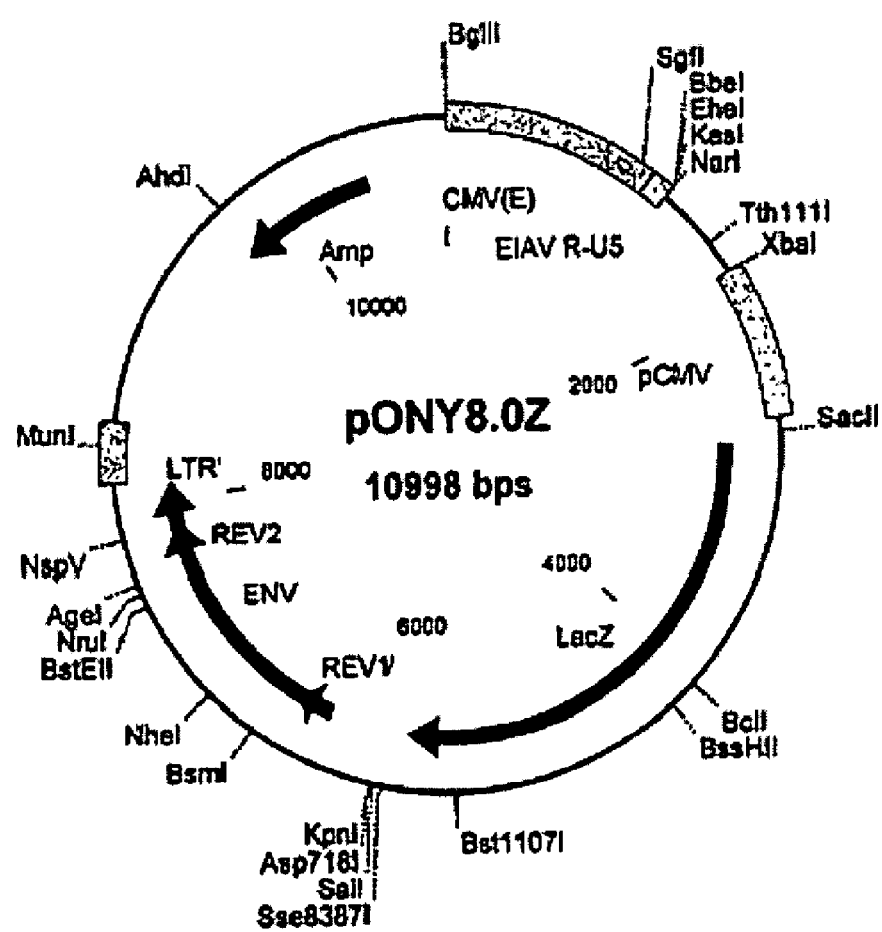
FIG. 4 shows a plasmid map of pONY8Z
Figure 5:
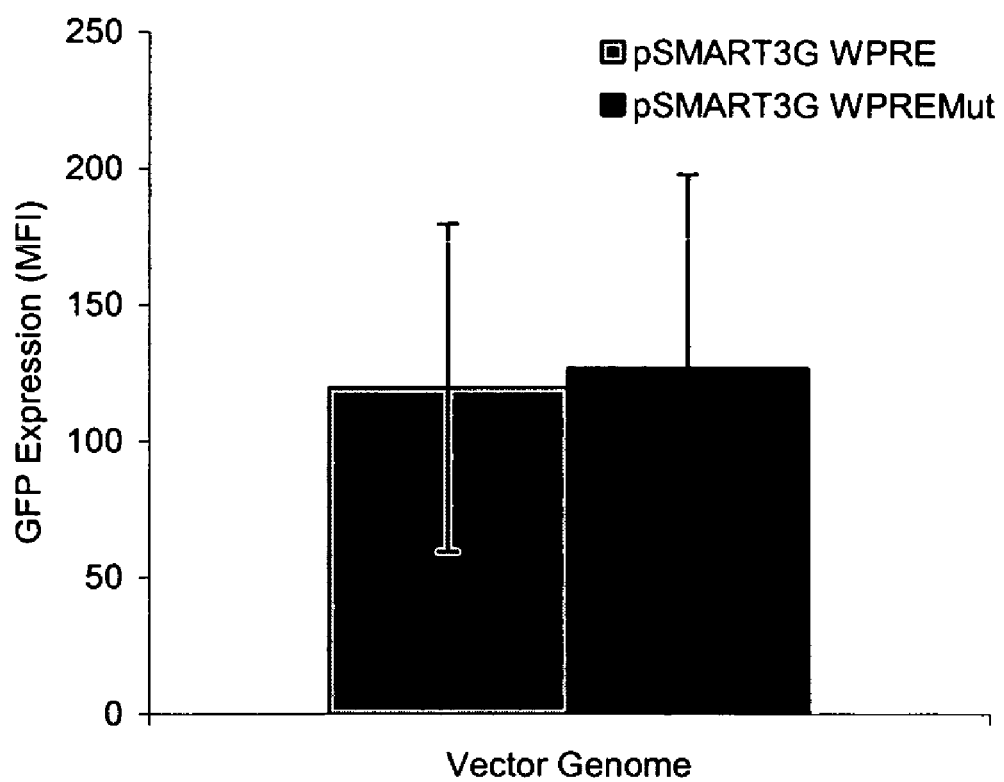
FIG. 5 shows the effect of mutations within the WPRE on the expression level of a reporter gene, GFP. FACS analysis was used to calculate the MFI of eGFP expression in D17 cells that were between 1% and 10% GFP-positive. The MFI±SD of eGFP expression in pSMART3G WPRE and pSMART3G WPREMut is shown.
Figure 7:
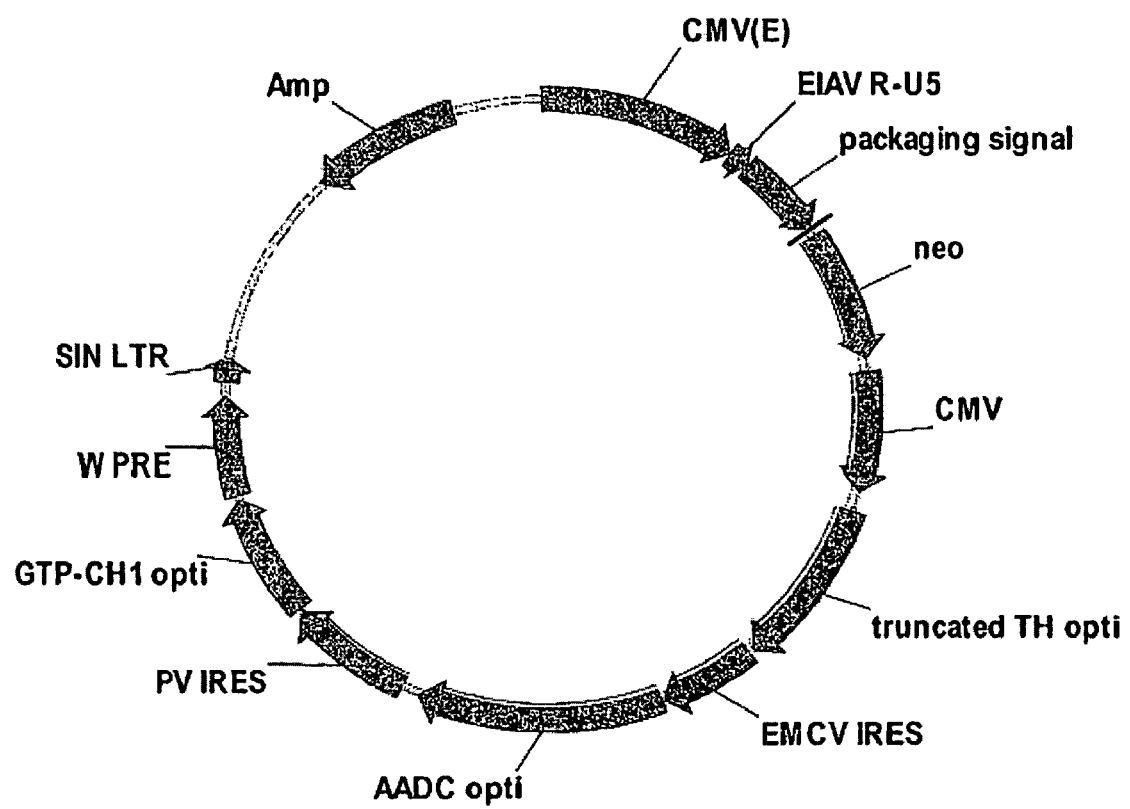
FIG. 7 shows a plasmid map of pONY8.9.4 MV optiY. This vector comprises a modified form of WPRE, at nucleotides 8206-8795 of the vector plasmid.

Various preferred features and embodiments of the present invention will now be described by way of non-limiting example. Although in general, the techniques mentioned herein are well known in the art, reference may be made in particular to Sambrook, et al., Molecular Cloning, A Laboratory Manual (1989) and Ausubel et al., Short Protocols in Molecular Biology (1999) 4$^{th}$ Ed., John Wiley & Sons, Inc. (as well as the complete version of Current Protocols in Molecular Biology).

As used herein, the term "operably linked" means that the components described are in a relationship permitting them to function in their intended manner.

Post-Transcriptional Regulatory Elements

The Woodchuck hepatitis virus (WHV) post-transcriptional regulatory element (WPRE) can enhance expression from a number of different vector types including lentiviral vectors (U.S. Pat. Nos. 6,136,597; 6,287,814; Zufferey, R., et al. (1999) J. Virol. 73: 2886-92). Without wanting to be bound by theory, this enhancement is thought to be due to improved RNA processing at the post-transcriptional level, resulting in increased levels of nuclear transcripts. A two-fold increase in mRNA stability also contributes to this enhancement (Zufferey, R., et al. ibid). The level of enhancement of protein expression from transcripts containing the WPRE versus those without the WPRE has been reported to be around 2-to-5 fold, and correlates well with the increase in transcript levels. This has been demonstrated with a number of different transgenes (Zufferey, R., et al. ibid).

The WPRE contains three cis-acting sequences important for its function in enhancing expression levels. In addition, it contains a fragment of approximately 180 bp comprising the 5'-end of the WHV X protein ORF (full length ORF is 425 bp), together with its associated promoter. Translation from transcripts initiated from the X promoter results in formation of a protein representing the NH$_2$-terminal 60 amino acids of the X protein. This truncated X protein can promote tumorigenesis, particularly if the truncated X protein sequence is integrated into the host cell genome at specific loci (Balsano, C. et al, (1991) Biochem. Biophys Res. Commun. 176: 985-92; Flajolet, M. et al, (1998) J. Virol. 72: 6175-80; Zheng, Y. W., et al, (1994) J. Biol. Chem. 269: 22593-8; Runkel, L., et al, (1993) Virology 197: 529-36). Therefore, expression of the truncated X protein could promote tumorigenesis if delivered to cells of interest, precluding safe use of wild-type WPRE sequences.

As used herein, the "X region" of the WPRE is defined as comprising at least the first 60-amino acids of the X protein ORF, including the translation initiation codon, and its associated promoter. A "functional" X protein is defined herein as a truncated X protein that is capable of promoting tumorigenesis, or a transformed phenotype, when expressed in cells of interest. A "non-functional" X protein in the context of this application is defined as an X protein that is incapable of promoting tumorigenesis in cells of interest.

The present inventors have introduced mutations into the WPRE sequence, and found that the mutations prevent expression of a functional X protein, thereby preventing tumorigenesis in the cells of interest. Preferably, these mutations are introduced into the promoter region of the X protein, or into the translation initiation codon of the X protein. The present inventors have found that the nature of these mutations, in addition to preventing expression of a functional X protein, also prevents the reversion back to the wild-type WPRE sequences, which can be accomplished by the low-fidelity proofreading activity of viral-encoded reverse transcriptase present in the vector genomes of the present invention.

A "mutation" can comprise one or more amino acid deletions, additions, or substitutions.

Accordingly, one aspect of the present invention provides an isolated nucleic acid molecule comprising a WPRE containing an X region, wherein the WPRE has a mutation in the X region whereby expression of a functional X protein is prevented. In preferred embodiments, the mutation is in the promoter sequence of the X region or in the initiation codon of the X region. Preferably, as a result of these mutations, the X protein is not expressed, or is non-functional.

Liver tumours can occur sporadically when vectors expressing the wild-type WPRE are transduced in utero. Despite the presence of the wild-type WPRE, tumours do not occur in the case of every integration event. Therefore, other secondary factors are presumably required to promote tumorigenesis. These secondary factors can include those arising from insertional mutagenesis as a result of integration of the viral vector genome comprising the wild-type WPRE. As a consequence, expression of a known factor that is involved in, but not sufficient for, tumorigenesis (for example, a mutated tumour suppressor gene) in the context of an integrating vector can lead to integration within, or adjacent to, a secondary gene that has a role in tumour generation and together with expression of the known factor, can lead to tumorigenesis. The tumour mass can then be removed and its genomic DNA isolated. Using this material, the integration site can be located and the unknown secondary factor can be identified. Location of the integration site can be achieved by standard methods known to the skilled artisan such as, but not limited to, Southern hybridisation and genomic PCR.

Therefore, in an embodiment of the present invention, methods for identifying a gene involved in tumorigenesis is provided, comprising the steps of introducing the isolated nucleic acid according to the first aspect of the invention, into a cell of interest, whereby the nucleic acid is recombined into chromosomal DNA of the cell of interest, determining whether the cell of interest forms a tumor; and, if the cell of interest forms a tumor: locating a site of recombination in the chromosomal DNA, and identifying a gene near or adjacent to the site of recombination, thereby identifying the gene involved in tumorigenesis.

Retroviruses

The concept of using viral vectors for gene therapy is well known (Verma and Somia (1997) Nature 389:239-242).

There are many retroviruses. For the present application, the term "retrovirus" includes: murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridae including lentiviruses.

A detailed list of retroviruses may be found in Coffin et al ("Retroviruses" 1997 Cold Spring Harbour Laboratory Press Eds: J M Coffin, S M Hughes, H E Varmus pp 758-763).

Lentiviruses also belong to the retrovirus family, but they can infect both dividing and non-dividing cells (Lewis et al (1992) EMBO J. 3053-3058).

The lentivirus group can be split into "primate" and "non-primate". Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

Details on the genomic structure of some lentiviruses may be found in the art. By way of example, details on HIV and EIAV may be found from the NCBI Genbank database (i.e. Genome Accession Nos. AF033819 and AF033820 respectively). Details of HIV variants may also be found in the HIV databases maintained by Los Alamos National Laboratory. Details of EIAV clones may be found at the NCBI database maintained by the National Institutes of Health.

During the process of infection, a retrovirus initially attaches to a specific cell surface receptor. On entry into the susceptible host cell, the retroviral RNA genome is then copied to DNA by the virally encoded reverse transcriptase, which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular genes. The provirus encodes the proteins and other factors required to make more virus, which can leave the cell by a process sometimes called "budding".

Each retroviral genome comprises genes called gag, pol and env, which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

For the viral genome, the site of transcription initiation is at the boundary between U3 and R in the left hand side LTR and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins. Some retroviruses have any one or more of the following genes that code for proteins that are involved in the regulation of gene expression: tat, rev, tax and rex.

With regard to the structural genes gag, pol and env themselves; gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome. The env gene encodes the surface (SU) glycoprotein and the transmembrane (TM) protein of the virion, which form a complex that interacts specifically with cellular receptor proteins. This interaction leads ultimately to infection by fusion of the viral membrane with the cell membrane.

Retroviruses may also contain "additional" genes, which code for proteins other than gag, pol and env. Examples of additional genes include in HIV, one or more of vif, vpr, vpx, vpu, tat, rev and nef. EIAV has, for example, the additional genes S2 and dUTPase.

Proteins encoded by additional genes serve various functions, some of which may be duplicative of a function provided by a cellular protein. In EIAV, for example, tat acts as a transcriptional activator of the viral LTR. It binds to a stable, stem-loop RNA secondary structure referred to as TAR. Rev regulates and co-ordinates the expression of viral genes through rev-response elements (RRE). The mechanisms of action of these two proteins are thought to be broadly similar to the analogous mechanisms in the primate viruses. The function of S2 is unknown. In addition, an EIAV protein, Ttm, has been identified that is encoded by the first exon of tat spliced to the env coding sequence at the start of the transmembrane protein.

Delivery Systems

Retroviral vector systems have been proposed as a delivery system for, inter alia, the transfer of a NOI to one or more sites of interest. The transfer can occur in vitro, ex vivo, in vivo, or combinations thereof. Retroviral vector systems have even been exploited to study various aspects of the retrovirus life cycle, including receptor usage, reverse transcription and RNA packaging (reviewed by Miller, 1992 Curr Top Microbiol Immunol 158:1-24).

A recombinant retroviral vector particle is capable of transducing a recipient cell with an NOI. Once within the cell, the RNA genome from the vector particle is reverse transcribed into DNA and integrated into the DNA of the recipient cell.

As used herein, the term "vector genome" refers to the RNA construct present in the retroviral vector particle and/or the integrated DNA construct. The term also embraces a separate or isolated DNA construct capable of encoding such an RNA genome. A retroviral or lentiviral genome should comprise at least one component part derivable from a retrovirus or a lentivirus. The term "derivable" is used in its normal sense as meaning a nucleotide sequence or a part thereof, which need not necessarily be obtained from a virus such as a lentivirus but instead could be derived therefrom. By way of example, the sequence may be prepared synthetically or by use of recombinant DNA techniques. Preferably the genome comprises a psi region (or an analogous component that is capable of causing encapsidation).

The viral vector genome is preferably "replication defective", by which we mean that the genome does not comprise sufficient genetic information alone to enable independent replication to produce infectious viral particles within the recipient cell. In a preferred embodiment, the genome lacks a functional env, gag or pol gene.

The viral vector genome may comprise some or all of the long terminal repeats (LTRs). Preferably the genome comprises at least part of the LTRs or an analogous sequence, which is capable of mediating proviral integration, and transcription. The sequence may also comprise or act as an enhancer-promoter sequence.

The viral vector genome of the second aspect of the invention may be provided as a kit of parts. For example, the kit may comprise (i) a plasmid or plasmids containing the NOIs and internal regulatory sequences, such as, for example, a promoter or an IRES sequence(s); and (ii) a retroviral genome construct with suitable restriction enzyme recognition sites for cloning the NOIs and internal regulatory sequence(s) into the viral genome.

It is known that the separate expression of the components required to produce a retroviral vector particle on separate DNA sequences cointroduced into the same cell will yield retroviral particles carrying defective retroviral genomes that carry therapeutic genes (e.g. Reviewed by Miller 1992). This cell is referred to as the producer cell (see below).

There are two common procedures for generating producer cells. In one, the sequences encoding retroviral Gag, Pol and Env proteins are introduced into the cell and stably integrated into the cell genome; a stable cell line is produced which is referred to as the packaging cell line. The packaging cell line produces the proteins required for packaging retroviral RNA but it cannot bring about encapsidation due to the lack of a psi region. However, when a vector genome having a psi region is introduced into the packaging cell line, the helper proteins can package the psi-positive recombinant vector RNA to produce the recombinant virus stock. This can be used to transduce the NOI into recipient cells. The recombinant virus whose genome lacks all genes required to make viral proteins can infect only once and cannot propagate. Hence, the NOI is introduced into the host cell genome without the generation of potentially harmful retrovirus. A summary of the available packaging lines is presented in "Retroviruses" (1997 Cold Spring Harbour Laboratory Press Eds: J M Coffin, S M Hughes, H E Varmus pp 449).

The present invention also provides a packaging cell line comprising a viral vector genome of the present invention. For example, the packaging cell line may be transduced with a viral vector system comprising the genome or transfected with a plasmid carrying a DNA construct capable of encoding the RNA genome. The present invention also provides a retroviral (or lentiviral) vector particle produced by such a cell.

The second approach is to introduce the three different DNA sequences that are required to produce a retroviral vector particle i.e. the env coding sequences, the gag-pol coding sequence and the defective retroviral genome containing one or more NOIs into the cell at the same time by transient transfection and the procedure is referred to as transient triple transfection (Landau & Littman 1992; Pear et al 1993). The triple transfection procedure has been optimised (Soneoka et al 1995; Finer et al 1994). WO 94/29438 describes the production of producer cells in vitro using this multiple DNA transient transfection method.

The components of the viral system, which are required to complement the vector genome, may be present on one or more "producer plasmids" for transfecting into cells.

The present invention also provides a vector system for producing a retrovirus-derived particle, comprising
  (i) a retroviral genome according to the second aspect of the invention;
  (ii) a nucleotide sequence coding for retroviral gag and pol proteins;
  (iii) nucleotide sequences encoding other essential viral packaging components not encoded by the nucleotide sequence of (ii).

Preferably, the nucleic acid sequence(s) encoding at least one of Vpr, Vif, Tat, Nef, or analogous auxiliary genes, from the retrovirus from which the particles are derived, are disrupted such as said nucleic acid sequence(s) are incapable of encoding functional Vpr, Vif, Tat, Nef, or analogous auxiliary proteins, or are removed from the system.

The present invention also provides a cell transfected with such a vector system and a retroviral vector particle produced by such a cell. Preferably the gag-pol sequence is codon optimised for use in the particular producer cell (see below).

The env protein encoded by the nucleotide sequence of iii) may be a homologous retroviral or lentiviral env protein. Alternatively, it may be a heterologous env, or an env from a non-retro or lentivirus (see below under "pseudotyping").

The term "viral vector system" is used generally to mean a kit of parts that can be used when combined with other necessary components for viral particle production to produce viral particles in host cells. For example, the retroviral vector genome may lack one or more of the genes needed for viral replication. This may be combined in a kit with a further complementary nucleotide sequence or sequences, for example on one or more producer plasmids. By cotransfection of the genome together with the producer plasmid(s), the necessary components should be provided for the production of infectious viral particles.

Alternatively, the complementary nucleotide sequence(s) may be stably present within a packaging cell line that is included in the kit.

The present invention also relates to a retroviral vector system, which is capable of delivering an RNA genome to a recipient cell, wherein the genome is longer than the wild type genome of the lentivirus. The vector system may, for example, be an EIAV vector system.

Preferably the RNA genome of the vector system has up to 5%, more preferably up to 10% or even up to 30% more bases than the wild-type genome. Preferably the RNA genome is about 10% longer than the wild-type genome. For example, wild type EIAV comprises an RNA genome of approximately 8 kb. An EIAV vector system of the present invention may have an RNA genome of up to (preferably about) 8.8 kb.

Preferably the retroviral vector system of the present invention is a self-inactivating (SIN) vector system.

By way of example, self-inactivating retroviral vector systems have been constructed by deleting the transcriptional enhancers or the enhancers and promoter in the U3 region of the 3' LTR. After a round of vector reverse transcription and integration, these changes are copied into both the 5' and the 3' LTRs, producing a transcriptionally inactive provirus. However, any promoter(s) internal to the LTRs in such vectors will still be transcriptionally active. This strategy has been employed to eliminate effects of the enhancers and promoters in the viral LTRs on transcription from internally placed genes. Such effects include increased transcription or suppression of transcription. This strategy can also be used to eliminate downstream transcription from the 3' LTR into genomic DNA. This is of particular concern in human gene therapy where it may be important to prevent the adventitious activation of an endogenous oncogene (Yu et al., (1986) PNAS 83: 3194-98; Marty et al., (1990) Biochimie 72: 885-7; Naviaux et al., (1996) J. Virol. 70: 5701-5; Iwakuma et al., (1999) Virol. 261: 120-32; Deglon et al., (2000) Human Gene Therapy 11: 179-90).

Preferably a recombinase-assisted mechanism is used, which facilitates the production of high titre regulated lentiviral vectors from the producer cells of the present invention.

As used herein, the term "recombinase assisted system" includes, but is not limited to, a system using the Cre recombinase/loxP recognition sites of bacteriophage P1 or the site-specific FLP recombinase of S. cerevisiae, which catalyses recombination events between 34 bp FLP recognition targets (FRTs).

The site-specific FLP recombinase of S. cerevisiae, which catalyses recombination events between 34 bp FLP recognition targets (FRTs), has been configured into DNA constructs to generate high level producer cell lines using recombinase-assisted recombination events (Karreman et al (1996) NAR 24:1616-1624). A similar system has been developed using the Cre recombinase/loxP recognition sites of bacteriophage P1 (Vanin et al (1997) J. Virol 71:7820-7826). This was configured into a lentiviral genome such that high titre lentiviral producer cell lines were generated.

By using producer/packaging cell lines, it is possible to propagate and isolate quantities of retroviral vector particles (e.g. to prepare suitable titres of the retroviral vector particles) for subsequent transduction of, for example, a site of interest (such as adult brain tissue). Producer cell lines are usually better for large-scale production or vector particles.

Transient transfection has numerous advantages over the packaging cell method. In this regard, transient transfection avoids the longer time required to generate stable vector-producing cell lines and is used if the vector genome or retroviral packaging components are toxic to cells. If the vector genome encodes toxic genes or genes that interfere with the replication of the host cell, such as inhibitors of the cell cycle or genes that induce apoptosis, it may be difficult to generate stable vector-producing cell lines, but transient transfection can be used to produce the vector before the cells die. Also, cell lines have been developed using transient infection that produce vector titre levels that are comparable to the levels obtained from stable vector-producing cell lines (Pear et al 1993, PNAS 90:8392-8396).

Producer cells/packaging cells can be of any suitable cell type. Producer cells are generally mammalian cells, but can be, for example, insect cells.

As used herein, the term "producer cell" or "vector producing cell" refers to a cell that contains all the elements necessary for production of retroviral vector particles.

Preferably, the producer cell is obtainable from a stable producer cell line.

Preferably, the producer cell is obtainable from a derived stable producer cell line.

Preferably, the producer cell is obtainable from a derived producer cell line.

As used herein, the term "derived producer cell line" is a transduced producer cell line that has been screened and selected for high expression of a marker gene. Such cell lines support high-level expression from the retroviral genome. The term "derived producer cell line" is used interchangeably with the term "derived stable producer cell line" and the term "stable producer cell line."

Preferably the derived producer cell line includes, but is not limited to, a retroviral and/or a lentiviral producer cell.

Preferably the derived producer cell line is an HIV or EIAV producer cell line, more preferably an EIAV producer cell line.

Preferably the envelope protein sequences, and nucleocapsid sequences are all stably integrated in the producer and/or packaging cell. However, one or more of these sequences could also exist in episomal form and gene expression could occur from the episome.

As used herein, the term "packaging cell" refers to a cell that contains those elements necessary for production of infectious recombinant virus that are lacking in the RNA genome. Typically, such packaging cells contain one or more producer plasmids, which are capable of expressing viral structural proteins (such as codon optimised gag-pol and env) but they do not contain a packaging signal.

The term "packaging signal" which is referred to interchangeably as "packaging sequence" or "psi" is used in reference to the non-coding, cis-acting sequence required for encapsidation of retroviral RNA strands during viral particle formation. In HIV-1, this sequence has been mapped to loci extending from upstream of the major splice donor site (SD) to at least the gag start codon.

Packaging cell lines suitable for use with the above-described vector constructs may be readily prepared (see also WO 92/05266), and utilised to create producer cell lines for the production of retroviral vector particles. As already mentioned, a summary of the available packaging lines is presented in "Retroviruses" (as above).

Also as discussed above, simple packaging cell lines, comprising a provirus in which the packaging signal has been deleted, have been found to lead to the rapid production of undesirable replication competent viruses through recombination. In order to improve safety, second-generation cell lines have been produced, wherein the 3' LTR of the provirus is deleted. In such cells, two recombinations would be necessary to produce a wild type virus. A further improvement involves the introduction of the gag-pol genes and the env gene on separate constructs so-called third generation packaging cell lines. These constructs are introduced sequentially to prevent recombination during transfection.

Preferably, the packaging cell lines are second-generation packaging cell lines.

Preferably, the packaging cell lines are third generation packaging cell lines.

In these split-construct, third generation cell lines, a further reduction in recombination may be achieved by changing the codons. This technique, based on the redundancy of the genetic code, aims to reduce homology between the separate constructs, for example, between the regions of overlap in the gag-pol and env open reading frames.

The packaging cell lines are useful for providing the gene products necessary to encapsidate and provide a membrane protein for a high titre vector particle production. The packaging cell may be a cell cultured in vitro, such as a tissue culture cell line. Suitable cell lines include, but are not limited to, mammalian cells, such as murine fibroblast derived cell lines or human cell lines. Preferably the packaging cell line is a primate or human cell line, such as for example: HEK293, 293-T, TE671, HT1080.

It is highly desirable to use high-titre virus preparations in both experimental and practical applictions. Techniques for increasing viral titre include using a psi plus packaging signal as discussed above and concentration of viral stocks.

As used herein, the term "high titre" means an effective amount of a retroviral vector or particle that is capable of transducing a target site such as a cell.

As used herein, the term "effective amount" means an amount of a retroviral or lentiviral vector or vector particle that is sufficient to induce expression of the NOIs at a target site.

A high-titre viral preparation for a producer/packaging cell is usually on the order of $10^5$ to $10^7$ retrovirus particles per ml. For transduction in tissues such as the brain, it is necessary to use very small volumes, so the viral preparation is concentrated by ultracentrifugation. The resulting preparation should have at least $10^8$ t.u./ml, preferably from $10^8$ to $10^9$ t.u./ml, more preferably at least $10^9$ t.u./ml. (The titer is expressed in transducing units per ml (t.u./ml) as titred on a standard D17 cell line). Other methods of concentration such as ultrafiltration or binding to and elution from a matrix may be used.

The expression products encoded by the NOIs may be proteins that are secreted from the cell. Alternatively, the NOI expression products are not secreted and are active within the cell. For some applications, it is preferred for the NOI expression product to demonstrate a bystander effect or a distant bystander effect; that is the production of the expression product in one cell leading to the modulation of additional, related cells, either neighbouring or distant (e.g. metastatic), which possess a common phenotype. Zennou et al., (2000) Cell 101: 173; Folleuzi et al., (2000) Nat. Genetics 25: 217; Zennou et al., (2001) Nat. Biotechnol. 19: 446.

The presence of a sequence termed the central polypurine tract (cPPT) may improve the efficiency of gene delivery to non-dividing cells. This cis-acting element is located, for example, in the EIAV polymerase coding region element. Preferably the genome of the present invention comprises a cPPT sequence.

In addition, the viral genome may comprise a translational enhancer.

The NOIs may be operatively linked to one or more promoter/enhancer elements. Transcription of one or more NOIs may be under the control of viral LTRs or alternatively promoter-enhancer elements. Preferably the promoter is a strong viral promoter such as CMV, or is a cellular constitutive promoter such as PGK, beta-actin or EF1alpha. The promoter may be regulated or tissue-specific. The control of expression can also be achieved by using such systems as the tetracycline system that switches gene expression on or off in response to outside agents (in this case tetracycline or its analogues).

Pseudotyping

In the design of retroviral vector systems, it is desirable to engineer particles with different target cell specificities to the native virus, to enable the delivery of genetic material to an expanded or altered range of cell types. One manner in which to achieve this is by engineering the virus envelope protein to alter its specificity. Another approach is to introduce a heterologous envelope protein into the vector particle to replace or add to the native envelope protein of the virus.

The term pseudotyping means incorporating in at least a part of, or substituting a part of, or replacing all of, an env gene of a viral genome with a heterologous env gene, for example, an env gene from another virus. Pseudotyping is not a new phenomenon and examples may be found in WO 99/61639, WO-A-98/05759, WO-A-98/05754, WO-A-97/17457, WO-A-96/09400, WO-A-91/00047 and Mebatsion et al 1997 Cell 90, 841-847.

In a preferred embodiment of the present invention, the vector system is pseudotyped with a gene encoding at least part of the rabies G protein. Examples of rabies G pseudotyped retroviral vectors may be found in WO99/61639. In a further preferred embodiment of the present invention, the vector system is pseudotyped with a gene encoding at least part of the VSV-G protein. Examples of VSV-G pseudotyped retroviral vectors may be found in U.S. Pat. No. 5,817,491.

It has been demonstrated that a retrovirus or lentivirus minimal system can be constructed from HIV, SIV, FIV, and EIAV viruses. Such a system requires none of the additional genes vif, vpr, vpx, vpu, tat, rev and nef for either vector production or for transduction of dividing and non-dividing cells. It has also been demonstrated that an EIAV minimal vector system can be constructed which does not require S2 for either vector production or for transduction of dividing and non-dividing cells. The deletion of additional genes is highly advantageous. Firstly, it permits vectors to be produced without the genes associated with disease in lentiviral (e.g. HIV) infections. In particular, tat is associated with disease. Secondly, the deletion of additional genes permits the vector to package more heterologous DNA. Thirdly, genes whose function is unknown, such as S2, may be omitted, thus reducing the risk of causing undesired effects. Examples of minimal lentiviral vectors are disclosed in WO-A-99/32646 and in WO-A-98/17815.

The absence of functional auxiliary genes from the retroviral vector production system means that those functional genes will also be absent from retroviral vector particles produced by the system. Also, any auxiliary proteins that would otherwise be encoded by those genes and incorporated into the vector particles will be absent from the vector particles. In known retroviral vector production systems, the auxiliary genes may be present as part of the vector genome-encoding DNA, or together with the packaging components. The location of an auxiliary gene in a vector production system depends in part on its relationship with other retroviral components. For example, vif is often part of a gag-pol packaging cassette in a packaging cell. Thus, to remove a functional auxiliary gene for the purposes of the invention may involve its removal from the packaging components, or from the vector genome, or perhaps both.

To remove a functional auxiliary gene may not require removal of the gene in its entirety. Usually removal of part of the gene, or disruption of the gene in some other way will be sufficient. The absence of a functional auxiliary gene is understood herein to mean that the gene is not present in a form in which it is capable of encoding the functional auxiliary protein.

In a preferred system according to the invention, functional vpr and tat genes or analogous genes normally present in the lentivirus on which the vector particles are based are both absent. These two auxiliary genes are associated with characteristics of lentiviruses that are particularly undesirable for a gene therapy vector. However, other than by the proviso given above, the invention is not limited with regard to the combination of auxiliary genes that are absent in a system according to the invention for producing HIV-1-based vector particles, any combination of three, or more preferably four, of the genes may be absent in their functional form. Most preferably, all five of the auxiliary genes vpr, vif, tat, nef, and vpu are absent in their functional form. Similarly, for systems concerned with other lentiviruses, it is most preferable that all of the auxiliary genes are absent in their functional form (except rev which is preferably present unless replaced by a system analogous to the rev/RRE system).

Thus, preferably, the delivery system used in the invention is devoid of at least tat and S2 (if it is an EIAV vector system), and possibly also vif, vpr, vpx, vpu and nef. More preferably, the systems of the present invention are also devoid of rev. Rev was previously thought to be essential in some retroviral genomes for efficient virus production. For example, in the case of HIV, it was thought that rev and RRE sequence should be included. However, it has been found that the requirement for rev and RRE can be reduced or eliminated by codon optimisation (see below) or by replacement with other functional equivalent systems such as the MPMV system. As expression of the codon-optimised gag-pol is rev-independent, RRE can be removed from the gag-pol expression cassette, thus removing any potential for recombination with any RRE contained on the vector genome.

In a preferred embodiment, the viral genome of the present invention lacks the Rev response element (RRE). In another preferred embodiment, a nucleic acid sequence encoding Rev, or a functional equivalent thereof, is disrupted such that the nucleic acid sequence is incapable of encoding the functional Rev or is removed from the vector genome.

In a preferred embodiment, the system used in the present invention is based on a so-called "minimal" system in which some or all of the additional genes have been removed. Preferably the viral vector of the present invention has a minimal viral genome.

As used herein, the term "minimal viral genome" means that the viral vector has been manipulated so as to remove the non-essential elements and to retain the essential elements to provide the required functionality to infect, transduce and deliver a NOI to a target host cell.

Preferably the viral vector with the minimal viral genome is a minimal lentiviral vector.

Codon Optimisation

Codon optimisation has previously been described in WO99/41397. Different cells differ in their usage of particular codons. This codon bias corresponds to a bias in the relative abundance of particular tRNAs in the cell type. By altering the codons in the sequence to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Codon optimisation has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. Codon optimisation also overcomes the Rev/RRE requirement for export, rendering optimised sequences Rev independent. Codon optimisation also reduces homologous recombination between different constructs within the vector system (for example, between the regions of overlap in the gag-pol and env open reading frames). The overall effect of codon optimisation is therefore a notable increase in viral titre and improved safety.

In one embodiment, only codons relating to INS are codon optimised. However, in a much more preferred and practical embodiment, the sequences are codon optimised in their entirety, with the exception of the sequence encompassing the frameshift site.

The gag-pol gene comprises two overlapping reading frames encoding gag and pol proteins respectively. The expression of both proteins depends on a frameshift during translation. This frameshift occurs as a result of ribosome "slippage" during translation. This slippage is thought to be caused at least in part by ribosome-stalling RNA secondary structures. Such secondary structures exist downstream of the frameshift site in the gag-pol gene. For HIV, the region of overlap extends from nucleotide 1222 downstream of the beginning of gag (wherein nucleotide 1 is the A of the gag ATG) to the end of gag (nt 1503). Consequently, a 281 bp fragment spanning the frameshift site and the overlapping region of the two reading frames is preferably not codon optimised. Retaining this fragment will enable more efficient expression of the gag-pol proteins.

For EIAV, the beginning of the overlap has been taken to be nt 1262 (where nucleotide 1 is the A of the gag ATG). The end of the overlap is at 1461 bp. To ensure that the frameshift site and the gag-pol overlap are preserved, the wild type sequence has been retained from nt 1156 to 1465.

Derivations from optimal codon usage may be made, for example, to accommodate convenient restriction sites, and conservative amino acid changes may be introduced into the gag-pol proteins.

In a highly preferred embodiment, codon optimisation was based on highly expressed mammalian genes. The third and sometimes the second and third base may be changed.

Due to the degenerate nature of the Genetic Code, it will be appreciated that a skilled worker can achieve numerous gag-pol sequences. Also, there are many retroviral variants described that can be used as a starting point for generating a codon optimised gag-pol sequence. Lentiviral genomes can be quite variable. For example, there are many quasi-species of HIV-1 that are still functional. This is also the case for EIAV. These variants may be used to enhance particular parts of the transduction process. Details of HIV variants may also be found in the HIV databases maintained by Los Alamos National Laboratory. Details of EIAV clones may be found at the NCBI database maintained by the National Institutes of Health.

The strategy for codon optimised gag-pol sequences can be used in relation to any retrovirus. This would apply to all lentiviruses, including EIAV, FIV, BIV, CAEV, VMR, SIV, HIV-1 and HIV-2. In addition, this method could be used to increase expression of genes from HTLV-1, HTLV-2, HFV, HSRV and human endogenous retroviruses (HERV), MLV and other retroviruses.

Codon optimisation can render gag-pol expression Rev independent. To enable the use of anti-rev or RRE factors in the retroviral vector, however, it would be necessary to render the viral vector generation system totally Rev/RRE independent. Thus, the genome also needs to be modified. This is achieved by optimising vector genome components. Advantageously, these modifications can also lead to the production of a safer system absent of all additional proteins both in the producer and in the transduced cell.

As described above, the packaging components for a retroviral vector include expression products of gag, pol and env genes. In addition, efficient packaging depends on a short sequence of 4 stem loops followed by a partial sequence from gag and env (the "packaging signal"). Thus, inclusion of a deleted gag sequence in the retroviral vector genome (in addition to the full gag sequence on the packaging construct) will optimise vector titre. To date, efficient packaging has been reported to require from 255 to 360 nucleotides of gag in vectors that still retain env sequences, or about 40 nucleotides of gag in a particular combination of splice donor mutation, gag and env deletions. It has surprisingly been found that a deletion of all but the N-terminal 360 nucleotides or so in gag leads to an increase in vector titre. Thus, preferably, the retroviral vector genome includes a gag sequence that comprises one or more deletions, more preferably the gag sequence comprises about 360 nucleotides derivable from the N-terminus.

NOIs

In the present invention, the term NOI (nucleotide sequence of interest) includes any suitable nucleotide sequence, which need not necessarily be a complete naturally occurring DNA or RNA sequence. Thus, the NOI can be, for example, a synthetic RNA/DNA sequence, a codon optimised RNA/DNA sequence, a recombinant RNA/DNA sequence (i.e. prepared by use of recombinant DNA techniques), a cDNA sequence or a partial genomic DNA sequence, including combinations thereof. The sequence need not be a coding region. If it is a coding region, it need not be an entire coding region. In addition, the RNA/DNA sequence can be in a sense orientation or in an anti-sense orientation. Preferably, it is in a sense orientation. Preferably, the sequence is, comprises, or is transcribed from cDNA.

The NOI(s), also referred to as "heterologous sequence(s)", "heterologous gene(s)" or "transgene(s)", may be any one or more of, for example, a selection gene(s), marker gene(s) and therapeutic gene(s).

The NOI may be a candidate gene that is of potential significance in a disease process. Thus the vector system of the present invention may, for example, be used for target validation purposes.

The NOI may have a therapeutic or diagnostic application. Suitable NOIs include, but are not limited to: sequences encoding enzymes, cytokines, chemokines, hormones, antibodies, anti-oxidant molecules, engineered immunoglobulin-like molecules, a single chain antibody, fusion proteins, immune co-stimulatory molecules, immunomodulatory molecules, anti-sense RNA, small interfering RNA (siRNA), a transdominant negative mutant of a target protein, a toxin, a conditional toxin, an antigen, a tumour suppresser protein and growth factors, membrane proteins, pro- and anti-angiogenic proteins and peptides, vasoactive proteins and peptides, anti-viral proteins and ribozymes, and derivatives thereof (such as with an associated reporter group). The NOIs may also encode pro-drug activating enzymes. When used in a research context, the NOIs may also encode reporter genes such as, but not limited to, green fluorescent protein (GFP), luciferase, β-galactosidase, or resistance genes to antibiotics such as, for example, ampicillin, neomycin, bleomycin, zeocin, chloramphenicol, hygromycin, kanamycin, among others.

The NOI may encode all or part of the protein of interest ("POI"), or a mutant, homologue or variant thereof. For example, the NOI may encode a fragment of the POI that is capable of functioning in vivo in an analogous manner to the wild-type protein.

The term "mutant" includes POIs that include one or more amino acid variations from the wild-type sequence. For example, a mutant may comprise one or more amino acid additions, deletions or substitutions.

Here, the term "homologue" means an entity having a certain homology with the NOI, or which encodes a protein having a degree of homology with the POI. Here, the term "homology" can be equated with "identity".

In the present context, a homologous sequence is taken to include an amino acid sequence that may be at least 75, 85 or 90% identical, preferably at least 95 or 98% identical to the subject sequence. Typically, the homologues will comprise the same active sites as the subject amino acid sequence. Although homology can also be considered in terms of similarity (i.e. amino acid residues having similar chemical properties/functions), in the context of the present invention, it is preferred to express homology in terms of sequence identity.

In the present context, a homologous sequence is taken to include a nucleotide sequence that may be at least 75, 85 or 90% identical, preferably at least 95 or 98% identical to the subject sequence. Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate percent (%) homology between two or more sequences.

A suitable computer program for carrying out sequence comparisons is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. The BLAST 2 Sequences tool is also available for comparing protein and nucleotide sequence (see FEMS Microbiol Lett 1999 174(2): 247-50; FEMS Microbiol Lett 1999 177(1): 187-8).

The sequences may also have deletions, insertions or substitutions of amino acid residues that produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| --- | --- | --- |
|  |  | I L V |
|  | Polar - uncharged | C S T M |
|  |  | N Q |
|  | Polar - charged | D E |
|  |  | K R |
| AROMATIC |  | H F W Y |

The present invention also encompasses homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another.

Preferably the NOI encodes a single POI or a mutant, homologue or variant thereof. In a highly preferred embodiment, the NOI does not encode a fusion protein. As used herein, the term "fusion protein" is used in its conventional sense to mean an entity that comprises two or more protein activities, joined together by a peptide bond to form a single chimeric protein. A fusion protein is encoded by a single polynucleotide driven by a single promoter.

Internal Ribosome Entry Site (IRES)

The viral genome of the present invention comprises at least one, but can optionally comprise two or more NOIs. In order for two or more NOIs to be expressed, there may be two or more transcription units within the vector genome, one for each NOI. However, it is clear from the literature that retroviral vectors achieve the highest titres and most potent gene expression properties if they are kept genetically simple (PCT/GB96/01230; Bowtell et al., 1988 J. Virol. 62, 2464; Correll et al., 1994 Blood 84, 1812; Emerman and Temin 1984 Cell 39, 459; Ghattas et al., 1991 Mol. Cell. Biol. 11, 5848; Hantzopoulos et al., 1989 PNAS 86, 3519; Hatzoglou et al., 1991 J. Biol. Chem 266, 8416; Hatzoglou et al., 1988 J. Biol. Chem 263, 17798; Li et al., 1992 Hum. Gen. Ther. 3, 381; McLachlin et al., 1993 Virol. 195, 1; Overell et al., 1988 Mol. Cell Biol. 8, 1803; Scharfman et al., 1991 PNAS 88, 4626; Vile et al., 1994 Gene Ther 1, 307; Xu et al., 1989 Virol. 171, 331; Yee et al., 1987 PNAS 84, 5197). Thus, it is preferable to use an internal ribosome entry site (IRES) to initiate translation of the second (and subsequent) coding sequence(s) in a poly-cistronic (or as used herein, "multicistronic") message (Adam et al 1991 J. Virol. 65, 4985).

Insertion of IRES elements into retroviral vectors is compatible with the retroviral replication cycle and allows expression of multiple coding regions from a single promoter (Adam et al (as above); Koo et al (1992) Virology 186:669-675; Chen et al 1993 J. Virol 67:2142-2148). IRES elements were first found in the non-translated 5' ends of picornaviruses where they promote cap-independent translation of viral proteins (Jang et al (1990) Enzyme 44: 292-309). When located between open reading frames in an RNA, IRES elements allow efficient translation of the downstream open reading frame by promoting entry of the ribosome at the IRES element followed by downstream initiation of translation.

As used herein, the term "cistron" refers to a nucleic acid segment corresponding to a polypeptide chain, comprising the relevant translational start (initiation) and stop (termination) codons. A multicistronic mRNA is an mRNA transcript with more than one cistron and thus, encoding more than one polypeptide.

A review on IRES is presented by Mountford and Smith (TIG May 1995 vol 11, No 5:179-184). A number of different IRES sequences are known including those from encephalomyocarditis virus (EMCV) (Ghattas, I. R., et al., Mol. Cell. Biol., 11:5848-5859 (1991); BiP protein [Macejak and Sarnow, Nature 353:91 (1991)]; the Antennapedia gene of Drosophila (exons d and e) [Oh, et al., Genes & Development, 6:1643-1653 (1992)] as well as those in poliovirus (PV) [Pelletier and Sonenberg, Nature 334: 320-325 (1988); see also Mountford and Smith, TIG 11, 179-184 (1985)].

According to WO-A-97/14809, IRES sequences are typically found in the 5' non-coding region of genes. In addition to those in the literature they can be found empirically by looking for genetic sequences that affect expression and then determining whether that sequence affects the DNA (i.e. acts as a promoter or enhancer) or only the RNA (acts as an IRES sequence).

IRES elements from PV, EMCV and swine vesicular disease virus have previously been used in retroviral vectors (Coffin et al, as above).

The term "IRES" includes any sequence or combination of sequences which work as or improve the function of an IRES.

The IRES(s) may be of viral origin (such as EMCV IRES, PV IRES, or FMDV 2A-like sequences) or cellular origin (such as FGF2 IRES, NRF IRES, Notch 2 IRES or EIF4 IRES).

For the IRES to be capable of initiating translation of each NOI, it should be located between or prior to NOIs in the vector genome. For example, for a multicistronic sequence containing n NOIs, the genome may be as follows:

[($NOI_1$-$IRES_1$)] ... $NOI_n$ n=1→n

For bi and tricistronic sequences, the order may be as follows:

$NOI_1$-$IRES_1$-$NOI_2$
$NOI_1$-$IRES_1$-$NOI_2$-$IRES_2$-$NOI_3$

Alternative configurations of IRESs and NOIs can also be utilised. For example transcripts containing the IRESs and NOIs need not be driven from the same promoter.

An example of this arrangement may be:

$IRES_1$-$NOI_1$-promoter-$NOI_2$-$IRES_2$-$NOI_3$.

Preferably, in any construct utilising an internal cassette having more than one IRES and NOI, the IRESs may be of different origins, that is, heterologous to one another. For example, one IRES may be from EMCV and the other IRES may be from poliovirus.

Other Methods of Expressing Multiple Genes from One Vector

Although IRESs are an efficient way to co-express multiple genes from one vector, other methods are also useful, and may be used alone or in conjunction with IRESs. These include the use of multiple internal promoters in the vector (Overell et al., Mol Cell Biol. 8: 1803-8 (1988)), or the use of alternate splicing patterns leading to multiple RNA species derived from the single viral genome that expresses the different genes. This strategy has previously been used by itself for two genes (Cepko et al. Cell 37: 1053 (1984)).

Transduced Cells

The present invention also relates to a cell that has been transduced with a vector system comprising a viral genome according to the first aspect of the invention.

The cell may be transduced in vivo, in vitro or ex vivo. For example, if the cell is a cell from a mammalian subject, the cell may be removed from the subject and transduced ready for reimplantation into the subject (ex vivo transduction). Alternatively, the cell may be transduced by direct gene transfer in vivo, using the vector system of the present invention in accordance with standard techniques (such as via injection of vector stocks expressing the NOIs). If the cell is part of a cell line that is stable in culture (i.e. which can survive numerous passages and can multiple in vitro) then it may be transduced in vitro by standard techniques, for example, by exposure of the cell to viral supernatants comprising vectors expressing the NOIs.

The cell may be any cell that is susceptible to transduction. If the vector system is capable of transducing non-dividing cells (for example if it is a lentiviral system) then the cell may be a non-dividing cell, such as a neuron.

Cassettes

The present invention can employ cassettes comprising one or more NOIs, which, in the case of two or more NOIs, can be operably linked by an IRES. These cassettes may be used in a method for producing the vector genome in a producer cell.

The present invention also provides an expression vector comprising such a cassette. Transfection of a suitable cell with such an expression vector should result in a cell that expresses each POI encoded by the NOI in the cassette. The present invention also provides such a transfected cell.

Cloning of the cassette into an expression vector and transfection of cells with the vector (to give expression of the cassette) can be carried out by techniques well known in the art (such as those described in Sambrook et al. (Molecular Cloning: A Laboratory Manual, 2nd Edition, Cold Spring Harbor Laboratory press (1989)), and other laboratory textbooks).

Preferably the cassette comprises a promoter. A cassette comprising two or more NOIs can be bicistronic or tricistronic, and can comprises the following elements:

Promoter-(NOI$_1$)-(IRES$_1$)-(NOI$_2$)
Promoter-(NOI$_1$)-(IRES$_1$)-(NOI$_2$)-(IRES$_2$)-(NOI$_3$)

Pharmaceutical Compositions

The present invention provides a pharmaceutical composition, which comprises a vector genome according to the second aspect of the invention and a pharmaceutically acceptable carrier, diluent or excipient (including combinations thereof).

The pharmaceutical compositions may be for human or animal usage in human and veterinary medicine or research, and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by both routes.

Where the pharmaceutical composition is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose or chalk, or in capsules or ovules either alone or in admixture with excipients, or in the form of elixirs, solutions or suspensions containing flavouring or colouring agents, or they can be injected parenterally, for example, intravenously, intramuscularly or subcutaneously. For parenteral administration, the compositions may be best used in the form of a sterile aqueous solution, which may contain other substances, for example, enough salts or monosaccharides to make the solution isotonic with blood. For buccal or sublingual administration, the compositions may be administered in the form of tablets or lozenges that can be formulated in a conventional manner.

Administration

Typically, a physician will determine the actual dosage that will be most suitable for an individual subject and it will vary with the age, weight and response of the particular patient and severity of the condition. The dosages below are exemplary of the average case. There can, of course, be individual instances where higher or lower dosage ranges are merited.

The compositions (or component parts thereof) of the present invention may be administered orally. In addition, or in the alternative, the compositions (or component parts thereof) of the present invention may be administered by direct injection. In addition, or in the alternative, the compositions (or component parts thereof) of the present invention may be administered topically. In addition, or in the alternative, the compositions (or component parts thereof) of the present invention may be administered by inhalation. In addition, or in the alternative, the compositions (or component parts thereof) of the present invention may also be administered by one or more of: parenteral, mucosal, intramuscular, intravenous, subcutaneous, intraocular or transdermal administration means, and are formulated for such administration.

By way of further example, the pharmaceutical composition of the present invention may be administered in accordance with a regimen of 1 to 10 times per day, such as once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The term "administered" also includes, but is not limited to, delivery by a mucosal route, for example, as a nasal spray or aerosol for inhalation or as an ingestible solution; a parenteral route where delivery is by an injectable form, such as, for example, an intravenous, intramuscular or subcutaneous route.

Hence, one or more of the following routes may administer the pharmaceutical composition of the present invention: oral administration, injection (such as direct injection), topical, inhalation, parenteral administration, mucosal administration, intramuscular administration, intravenous administration, subcutaneous administration, intraocular administration or transdermal administration.

Diseases

Pharmaceutical compositions comprising an effective amount of vector comprising an identified modulating moiety operably linked to an NOI may be used in the treatment of disorders, such as those listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; diseases associated with viruses and/or other intracellular pathogens; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillain-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue. Specific cancer related disorders include but not limited to: solid tumours; blood born tumours such as leukemias; tumor metastases; benign tumours, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; wound granulation; coronary collaterals; cerebral collaterals; arteriovenous malformations; ischaemic limb angiogenesis; neovascular glaucoma; retrolental fibroplasia; diabetic neovascularization; *Helicobacter*-related diseases, fractures, vasculogenesis, hematopoiesis, ovulation, menstruation and placentation.

Various preferred features and embodiments of the present invention will now be described in more detail by way of non-limiting examples.

EXAMPLES

Example 1

Alterations to the Woodchuck Hepatitis Virus Post-Transcriptional Regulatory Element (WPRE) to Increase the Safety Profile of Viral Vectors A study was conducted to evaluate administration of our EIAV vectors via the main artery to foetal mice in utero. After birth, the mice were monitored for long periods. Mice transduced with an EIAV vector containing the wild-type WPRE (pSMART2 and 3) developed liver tumours while vectors that did not contain the WPRE (pONY8 series) did not. The tumours were associated only with the liver, and were not observed in other organs. Use of the pSMART2Z vector led to development of liver tumours within 3 months of birth. The results indicate that the presence of a WPRE with the wild-type nucleotide sequence often resulted in the development of liver tumours following in utero administration of vector. This may be due to effects resulting from partial functioning of the X promoter and truncated X-polypeptide. This is a surprising observation given that the X-protein promoter requires WHV proteins to function fully. Insertion of the WPRE in retroviral or lentiviral vectors in the reverse orientation leads to a reduction in protein expression, as measured by marker gene expression studies (Zufferey, R., et al, (1999) J. Virol. 73: 2886-92). The mechanism for this inhibition may be due to antisense effects resulting from transcription from the X promoter (Zufferey, R., et al, ibid). Therefore, it is possible that low-level transcription from the X promoter leads to accumulation of a truncated X protein polypeptide that contributes to the formation of liver tumours.

Given this observation, the ability of the WPRE to express the X-protein would need to be abrogated. To achieve this, mutation of nucleotides within the X promoter region, or within the translation initiation codon (ATG) of the X protein itself, or preferably both could be introduced. Maximal diversity from the wild type WPRE sequence would be the preferred option, as this will prevent reversion to wild-type sequence from occurring.

Given that the retroviral reverse transcriptase (in this case originating from the lentivirus, EIAV) has a low fidelity (an average single mistake incorporated per 10,000 nucleotides reverse transcribed), then the likelihood of a single base pair change reverting an altered nucleotide back to wild type will occur at a frequency of 1 per 40,000 integration events. Therefore, with each change relative to the wild-type WPRE sequence comes an additive reduction in the likely reversion to functional wild-type sequence. However, balanced with the desire to maximise diversity from the wild-type sequence is the need to retain WPRE functionality: there are presumably a limited number of changes that can be made to the WPRE without affecting its ability to enhance transgene expression.

A set of nucleotide changes within the WPRE that maintain its positive effects on transgene expression is provided, while dramatically lowering the probability of reversion to wild type. This altered WPRE sequence is referred to as WPREMut (SEQ ID NO:1).

The mutations were inserted by overlap PCR using the following primers:

WPRE, or WPREMut was conducted. Transductions of D17 cells were conducted using dilutions of the vector preps and pooled transduced cells were analysed for eGFP expression by FACS from each dilution. Samples containing between 1% and 10% GFP-positive cells were used in order to compare the expression level of GFP, in order to control for differences in vector titre. The mean fluorescence intensity (MFI) of eGFP expression for each of these samples was used; the average MFI±SD is shown in FIG. 5.

The sum of the 13 changes within the WPREMut relative to wild-type WPRE is predicted to reduce the probability of reversion to wild-type sequence to a very small level. FIG. 6 shows an alignment of WPRE sequences showing the mutations that have been introduced into the WPRE.

To study the effects of using the WPRE with introduced changes (WPREMut) in a relevant system, a study will compare vectors containing the wild-type WPRE and those containing the mutated WPRE. To achieve this, the WPRE in pSMART2Z has been swapped with the WPREMut sequence to create pSMART2ZWPREMut. These two vectors were made in parallel using the same production process (co-transfection of HEK293T cells with pONY3.1 (wild-type Gag/Pol expression construct) and pRV67 (VSV-G expression construct). In addition to these two vectors, a latest generation EIAV vector genome will be tested in parallel (pONYT9.1NCZ). This vector genome differs from pSMART2Z in a number of ways (in addition to the WPREMut sequence): i) a tetracycline resistance gene replacing the ampicillin resistance gene in earlier vector genomes (eg. pSMART2Z); ii) mutations within the major splice donor site to prevent unwanted splicing; iii) mutations within the initiation codon of the first exon of EIAV Tat (CTG) to prevent translation of the truncated Tat polypeptide; iv) mutations of all the ATG sequences within the packaging signal to ATTG (Ψ; pSMART2Z vectors contained the first two ATG sequences mutated in this fashion); v) a neomycin transferase gene downstream of the Ψ site that allows production of high titre vector in the absence of Rev; vi) minimal retained nucleotide sequence corresponding to a small region of EIAV env (pSMART2 vectors contain a larger fragment from this region of EIAV). The pONYT9.1NCZ vector is made by transient transfection of HEK293T cells with pESGPK (the codon optimised Gag/Pol expression construct, with a kanamycin resistance gene) and pRVK (a kanamycin resistant variant of pRV67, the VSV-G expression construct). The vectors to be compared in this study are summarised in Table 1.

```
1. 5'-GTG AAT TCG CGG CCG CAA TCA ACC TCT                 (SEQ ID NO:8)

2. 5'-GGT GGC AAC ACA GGC GAG CAG CCC CGA GTC TCA GCA GAC (SEQ ID NO:9)
   CTT CCC CGA CAA C 3. 5'-CCG TGG TGT TGT CGG GGA AGG TCT GCT GAG ACT CGG     (SEQ ID NO:10)

4. 5'-GCT GTC GAG CGG CCG CGA ATT CAC TAG TGA TTC TCG AC  (SEQ ID NO:11)
```

Primers 1 and 2 were used to amplify a 452 bp PCR product using the wild-type WPRE sequence as template (PCR#1). Primers 3 and 4 were used to amplify a 260 bp PCR product using the wild-type WPRE sequence as template (PCR#2). PCR#1 and PCR#2 were used in overlap PCR to create WPREMut (652 bp). WPREMut was inserted into vector genomes using the flanking Not I sites.

A comparison of the expression of a reporter gene (eGFP) from pSMART3G vectors containing either wild-type Mice will be treated as for the previous study (administration of test article via the main artery to foetal mice in utero) and observed for extended periods for the generation of tumours. The results of this study will demonstrate whether the wild-type WPRE sequence is indeed responsible for the generation of tumours in this model. These results will provide evidence supporting the use of vectors containing the improved WPRE (WPREMut) rather than wild-type WPRE in vivo.

TABLE 1

Vectors to be used in comparative study of EIAV vectors in the murine in utero transduction model.

| Test article | Vector genome | Gag/Pol expression cassette | VSV-G expression cassette | WPRE (WT/Mut) |
|---|---|---|---|---|
| 1 | pSMART2Z | pONY3.1 | pRV67 | WT |
| 2 | pSMART2Z WPREMut | pONY3.1 | pRV67 | Mut |
| 3 | pONYT9.1NCZ | pESGPK | pRVK | Mut |
| 4 | Formulation buffer | N/A | N/A | N/A |

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

What is claimed is:

1. An isolated nucleic acid molecule comprising a woodchuck post-transcriptional regulatory element (WPRE) containing an X region, wherein the WPRE has a mutation in the X region whereby expression of a functional X protein is prevented, and wherein the nucleic acid molecule comprises the sequence of SEQ ID NO: 1.

2. An isolated nucleic acid molecule comprising a woodchuck post-transcriptional regulatory element (WPRE) containing an X region, wherein the WPRE has a mutation in the X region whereby expression of a functional X protein is prevented, wherein the X region comprises a promoter sequence, and wherein the mutation is in the promoter sequence.

3. An isolated nucleic acid molecule comprising a woodchuck post-transcriptional regulatory element (WPRE) containing an X region, wherein the WPRE has a mutation in the X region whereby expression of a functional X protein is prevented, and wherein the X region comprises an initiation codon and wherein the mutation is in the initiation codon.

4. A retroviral vector genome comprising at least one nucleotide of interest (NOI) and the nucleic acid molecule of claim 1, 2, or 3.

5. The retroviral vector genome of claim 4, which is a lentiviral vector genome.

6. The retroviral vector genome of claim 4, wherein the retroviral vector genome comprises a self-inactivating (SIN) LTR.

7. The retroviral vector genome of claim 4, wherein the retroviral vector genome is multicistronic.

8. A retroviral vector system for producing a retroviral vector particle, comprising:
   (i) the retroviral vector genome of claim 4;
   (ii) a nucleotide sequence encoding retroviral gag and pol proteins; and
   (iii) nucleotide sequences encoding other essential viral packaging components not encoded by the nucleotide sequence of ii).

9. A composition comprising the retroviral vector genome of claim 4, together with a carrier or diluent.

10. A method of delivering at least one nucleotide sequence of interest (NOI) to a target cell, comprising introducing the retroviral vector genome of claim 8 into the target cell, whereby the NOL is delivered to the target cell.

11. The lentiviral vector genome of claim 5, which is a minimal lentiviral vector genome.

12. The lentiviral vector genome according to claim 5, wherein a nucleic acid sequence encoding Rev is disrupted such that the nucleic acid sequence is incapable of encoding functional Rev or the nucleic acid sequence encoding Rev is removed from the vector genome.

13. The lentiviral vector genome according to claim 5, wherein a nucleic acid sequence encoding Tat is disrupted such that the nucleic acid sequence is incapable of encoding functional Tat or the nucleic acid sequence encoding Tat is removed from the lentiviral vector genome.

14. The lentiviral vector genome of claim 5, wherein the lentiviral vector genome is from a viral species selected from the group consisting of human immunodeficiency virus (HIV), simian immunodeficiency virus (SIV), visna/maedi virus (VMV), caprine arthritis-encephalitis virus (CAEV), equine infectious anaemia virus (EIAV), feline immunodeficiency virus (FIV) and bovine immunodeficiency virus (BIV).

15. The lentiviral vector genome of claim 5, wherein the lentiviral vector genome is from a non-primate lentivirus.

16. The lentiviral vector genome of claim 5, wherein the lentiviral vector genome comprises a central polypurine tract (cPPT) sequence.

17. The lentiviral vector genome of claim 5, wherein the lentiviral vector genome comprises a gag packaging signal having ATG motifs, and wherein the ATG motifs are ATTG motifs.

18. The retroviral vector genome of claim 7, wherein the retroviral vector genome comprises at least one internal regulatory element.

19. The retroviral vector genome of claim 18, wherein the internal regulatory element is a promoter or an internal ribosomal entry site (IRES).

20. The retroviral vector system of claim 8, wherein the retroviral vector system is a lentiviral vector system, and wherein nucleic acid sequence(s) encoding at least one of Vpr, Vif, Tat, Nef, or analogous lentiviral auxiliary proteins are disrupted such that the nucleic acid sequence(s) are incapable of encoding functional Vpr, Vif, Tat, Nef, or the nucleic acid sequence(s) encoding Vpr, Vif, Tat, Nef, or analogous auxiliary proteins are removed from the lentiviral vector system.

21. The retroviral vector system of claim 8, wherein the vector system is pseudotyped with at least part of a heterologous env protein.

22. A retroviral particle produced from the retroviral vector system of claim 8.

23. An isolated cell that has been transduced with the retroviral vector system of claim 8.

24. The retroviral vector system of claim 21, wherein the heterologous env protein is from Rabies-G or VSV-G.

25. A composition comprising the viral particle of claim 22, together with a carrier or diluent.

26. A retroviral vector comprising at least one nucleotide sequence of interest (NOI) and a nucleic acid molecule comprising a woodchuck post-transcriptional regulatory element (WPRE) containing an X region, wherein the WPRE has a mutation in the X region whereby expression of a functional X protein is prevented, and wherein the nucleic acid molecule comprises the sequence of SEQ ID NO: 1.

27. A retroviral vector comprising at least one nucleotide sequence of interest (NOI) and a nucleic acid molecule comprising a woodchuck post-transcriptional regulatory element (WPRE) containing an X region, wherein the WPRE has a mutation in the X region whereby expression of a functional X protein is prevented, wherein the X region comprises a promoter sequence, and wherein the mutation is in the promoter sequence.

28. A retroviral vector comprising at least one nucleotide sequence of interest (NOI) and a nucleic acid molecule comprising a woodchuck post-transcriptional regulatory element (WPRE) containing an X region, wherein the WPRE has a mutation in the X region whereby expression of a functional X protein is prevented, wherein the X region comprises an initiation codon and wherein the mutation is in the initiation codon.

29. A method of making a retroviral particle comprising the steps of:
  (i) introducing the retroviral vector of claim 26, 27, or 28 into a packaging cell, or introducing the retroviral vector of claim 26, 27, or 28 together with nucleic acid sequence(s) encoding gag/pol and envelope proteins into a producer cell; and
  (ii) obtaining the retroviral vector particle therefrom, wherein said retroviral vector particle comprises the at least one NOI and the nucleic acid molecule comprising the mutated WPRE.

30. A method of delivering at least one NOI to a target cell, comprising introducing the retroviral vector of claim 26, 27, or 28 into the target cell, whereby the NOI is delivered to the target cell.

31. The method of claim 29, wherein the envelope is a heterologous envelope protein selected from the group consisting of Rabies G and VSV-G.

\* \* \* \* \*

UNITED STATES PATENT AND TRADEMARK OFFICE
CERTIFICATE OF CORRECTION

PATENT NO.         : 7,419,829 B2                                Page 1 of 1
APPLICATION NO.    : 10/873573
DATED              : September 2, 2008
INVENTOR(S)        : Kyri Mitrophanous et al.

It is certified that error appears in the above-identified patent and that said Letters Patent is hereby corrected as shown below:

Title Page

(75)   Inventors: Kyri Mitrophanous, Oxford (GB); Jonathan Rohll, Oxford (GB);

James Miskin, Oxford (GB); "Susan Marie," should read --Susan Mary,--

Kingsman, Oxford (GB)

Signed and Sealed this

Thirty-first Day of March, 2009

JOHN DOLL
*Acting Director of the United States Patent and Trademark Office*

SEQUENCE LISTING

```
<160> NUMBER OF SEQ ID NOS: 11

<210> SEQ ID NO 1
<211> LENGTH: 593
<212> TYPE: DNA
<213> ORGANISM: Woodchuck hepatitis virus

<400> SEQUENCE: 1
aatcaacctc tggattacaa aaatttgtga aagattgact ggtattctta actatgttgc    60
tccttttacg ctatgtggat acgctgcttt aatgcctttg tatcatgcta ttgcttcccg   120
tatggctttc attttctcct ccttgtataa atcctggttg ctgtctcttt atgaggagtt   180
gtggcccgtt gtcaggcaac gtggcgtggt gtgcactgtg tttgctgacg caaccccac    240 tggttggggc attgccacca cctgtcagct cctttccggg actttcgctt tccccctccc   300
tattgccacg gcggaactca tcgccgcctg ccttgcccgc tgctggacag gggctcggct   360
gttgggcact gacaattccg tggtgttgtc ggggaaggtc tgctgagact cggggctgct   420
cgcctgtgtt gccacctgga ttctgcgcgg gacgtccttc tgctacgtcc cttcggccct   480
caatccagcg gaccttcctt cccgcggcct gctgccggct ctgcggcctc ttccgcgtct   540
tcgccttcgc cctcagacga gtcggatctc cctttgggcc gcctccccgc ctg          593

<210> SEQ ID NO 2
<211> LENGTH: 18
<212> TYPE: DNA
<213> ORGANISM: Woodchuck hepatitis virus

<400> SEQUENCE: 2
gtctgctgag agactcgg                                                   18

<210> SEQ ID NO 3
<211> LENGTH: 21
<212> TYPE: DNA
<213> ORGANISM: Woodchuck hepatitis virus

<400> SEQUENCE: 3
ggggaagctg acgtcctttc c                                               21

<210> SEQ ID NO 4
<211> LENGTH: 20
<212> TYPE: DNA
<213> ORGANISM: Woodchuck hepatitis virus

<400> SEQUENCE: 4
gggaaggtct gctgagactc                                                 20
```

<210> SEQ ID NO 5
<211> LENGTH: 592
<212> TYPE: DNA
<213> ORGANISM: Woodchuck hepatitis virus

<400> SEQUENCE: 5

| | | | | | |
|---|---|---|---|---|---|
| aatcaacctc | tggattacaa | aatttgtgaa | agattgactg | gtattcttaa | ctatgttgct | 60 |
| ccttttacgc | tatgtggata | cgctgcttta | atgcctttgt | atcatgctat | tgcttcccgt | 120 |
| atggctttca | ttttctcctc | cttgtataaa | tcctggttgc | tgtctcttta | tgaggagttg | 180 |
| tggcccgttg | tcaggcaacg | tggcgtggtg | tgcactgtgt | ttgctgacgc | aaccccact | 240 |
| ggttggggca | ttgccaccac | ctgtcagctc | ctttccggga | ctttcgcttt | ccccctccct | 300 |
| attgccacgg | cggaactcat | cgccgcctgc | cttgcccgct | gctggacagg | ggctcggctg | 360 |
| ttgggcactg | acaattccgt | ggtgttgtcg | gggaagctga | cgtcctttcc | atggctgctc | 420 |
| gcctgtgttg | ccacctggat | tctgcgcggg | acgtccttct | gctacgtccc | ttcggccctc | 480 |
| aatccagcgg | accttccttc | ccgcggcctg | ctgccggctc | tgcggcctct | tccgcgtctt | 540 |
| cgccttcgcc | ctcagacgag | tcggatctcc | ctttgggccg | cctccccgcc | tg | 592 |

<210> SEQ ID NO 6
<211> LENGTH: 593
<212> TYPE: DNA
<213> ORGANISM: Woodchuck hepatitis virus

<400> SEQUENCE: 6

| | | | | | |
|---|---|---|---|---|---|
| aatcaacctc | tggattacaa | aaatttgtga | agattgactg | gtattcttaa | actatgttgc | 60 |
| tccttttacg | ctatgtggat | acgctgcttt | aatgcctttg | tatcatgcta | ttgcttcccg | 120 |
| tatggctttc | attttctcct | ccttgtataa | atcctggttg | ctgtctcttt | atgaggagtt | 180 |
| gtggcccgtt | gtcaggcaac | gtggcgtggt | gtgcactgtg | tttgctgacg | caaccccac | 240 |
| tggttggggc | attgccacca | cctgtcagct | cctttccggg | actttcgctt | tccccctccc | 300 |
| tattgccacg | gcggaactca | tcgccgcctg | ccttgcccgc | tgctggacag | gggctcggct | 360 |
| gttgggcact | gacaattccg | tggtgttgtc | ggggaagctg | acgtcctttc | catggctgct | 420 |
| cgcctgtgtt | gccacctgga | ttctgcgcgg | gacgtccttc | tgctacgtcc | cttcggccct | 480 |
| caatccagcg | gaccttcctt | cccgcggcct | gctgccggct | ctgcggcctc | ttccgcgtct | 540 |
| tcgccttcgc | cctcagacga | gtcggatctc | cctttgggcc | gcctccccgc | ctg | 593 |

<210> SEQ ID NO 7
<211> LENGTH: 11622
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 7

| | | | | | |
|---|---|---|---|---|---|
| tttgagattt | ctgtcgccga | ctaaattcat | gtcgcgcgat | agtggtgttt | atcgccgata | 60 |
| gagatggcga | tattggaaaa | attgatattt | gaaaatatgg | catattgaaa | atgtcgccga | 120 |
| tgtgagtttc | tgtgtaactg | atatcgccat | ttttccaaaa | gtgattttg | ggcatacgcg | 180 |
| atatctggcg | atagcgctta | tcgtttac | ggggatggc | gatagacgac | tttggtgact | 240 |
| tgggcgattc | tgtgtgtcgc | aaatatcgca | gtttcgatat | aggtgacaga | cgatatgagg | 300 |
| ctatatcgcc | gatagaggcg | acatcaagct | ggcacatggc | caatgcatat | cgatctatac | 360 |

```
attgaatcaa tattggccat tagccatatt attcattggt tatatagcat aaatcaatat    420
tggctattgg ccattgcata cgttgtatcc atatcgtaat atgtacattt atattggctc    480
atgtccaaca ttaccgccat gttgacattg attattgact agttattaat agtaatcaat    540
tacggggtca ttagttcata gcccatatat ggagttccgc gttacataac ttacggtaaa    600
tggcccgcct ggctgaccgc ccaacgaccc ccgcccattg acgtcaataa tgacgtatgt    660
tcccatagta acgccaatag ggactttcca ttgacgtcaa tgggtggagt atttacggta    720
aactgcccac ttggcagtac atcaagtgta tcatatgcca gtccgcccc ctattgacgt     780
caatgacggt aaatggcccg cctggcatta tgcccagtac atgaccttac gggactttcc    840
tacttggcag tacatctacg tattagtcat cgctattacc atggtgatgc ggttttggca    900
gtacaccaat gggcgtggat agcggtttga ctcacgggga tttccaagtc tccacccat    960
tgacgtcaat gggagtttgt tttggcacca aaatcaacgg gactttccaa aatgtcgtaa   1020
caactgcgat cgcccgcccc gttgacgcaa atgggcggta ggcgtgtacg gtgggaggtc   1080
tatataagca gagctcgttt agtgaaccgg gcactcagat tctgcggtct gagtcccttc   1140
tctgctgggc tgaaaaggcc tttgtaataa atataattct ctactcagtc cctgtctcta   1200
gtttgtctgt tcgagatcct acagttggcg cccgaacagg gacctgagag gggcgcagac   1260
cctacctgtt gaacctggct gatcgtagga tccccgggac agcagaggag aacttacaga   1320
agtcttctgg aggtgttcct ggccagaaca caggaggaca ggtaagattg ggagaccctt   1380
tgacattgga gcaaggcgct caagaagtta gagaaggtga cggtacaagg gtctcagaaa   1440
ttaactactg gtaactgtaa ttgggcgcta agtctagtag acttatttca ttgataccaa   1500
ctttgtaaaa gaaaaggact ggcagctgag ggattgtcat tccattgctg gaagattgta   1560
actcagacgc tgtcaggaca agaaagagag gcctttgaaa gaacattggt gggcaatttc   1620
tgctgtaaag attgggcctc cagattaata attgtagtag attggaaagg catcattcca   1680
gctcctaaga gcgaaatatt gaaaagaaga ctgctaataa aaagcagtct gagccctctg   1740
aagaatatct ctagaactag tggatccccc gggccaaaac ctagcgccac catgattgaa   1800
caagatggat tgcacgcagg ttctccggcc gcttgggtgg agaggctatt cggctatgac   1860
tgggcacaac agacaatcgg ctgctctgat gccgccgtgt tccggctgtc agcgcagggg   1920
cgcccggttc ttttttgtcaa gaccgacctg tccggtgccc tgaatgaact gcaggacgag   1980
gcagcgcggc tatcgtggct ggccacgacg ggcgttcctt gcgcagctgt gctcgacgtt   2040
gtcactgaag cgggaaggga ctggctgcta ttgggcgaag tgccggggca ggatctcctg   2100
tcatctcacc ttgctcctgc cgagaaagta tccatcatgg ctgatgcaat gcggcggctg   2160
catacgcttg atccggctac ctgcccattc gaccaccaag cgaaacatcg catcgagcga   2220
gcacgtactc ggatggaagc cggtcttgtc gatcaggatg atctggacga agagcatcag   2280
gggctcgcgc cagccgaact gttcgccagg ctcaaggcgc gcatgcccga cggcgaggat   2340
ctcgtcgtga cccatggcga tgcctgcttg ccgaatatca tggtggaaaa tggccgcttt   2400
tctggattca tcgactgtgg ccggctgggt gtggcggacc gctatcagga catagcgttg   2460
gctacccgtg atattgctga agagcttggc ggcgaatggg ctgaccgctt cctcgtgctt   2520
tacggtatcg ccgctcccga ttcgcagcgc atcgccttct atcgccttct tgacgagttc   2580
ttctgagcgg gccgcgaattc aaaagctaga gtcgactcta gggagtgggg aggcacgatg   2640
gccgctttgg tcgaggcgga tccggccatt agccatatta ttcattggtt atatagcata   2700
```

```
aatcaatatt ggctattggc cattgcatac gttgtatcca tatcataata tgtacattta    2760
tattggctca tgtccaacat taccgccatg ttgacattga ttattgacta gttattaata    2820
gtaatcaatt acggggtcat tagttcatag cccatatatg gagttccgcg ttacataact    2880
tacggtaaat ggcccgcctg gctgaccgcc caacgacccc cgcccattga cgtcaataat    2940
gacgtatgtt cccatagtaa cgccaatagg gactttccat tgacgtcaat gggtggagta    3000
tttacggtaa actgcccact tggcagtaca tcaagtgtat catatgccaa gtacgccccc    3060
tattgacgtc aatgacggta aatggcccgc ctggcattat gcccagtaca tgaccttatg    3120
ggactttcct acttggcagt acatctacgt attagtcatc gctattacca tggtgatgcg    3180
gttttggcag tacatcaatg ggcgtggata gcggtttgac tcacggggat ttccaagtct    3240
ccaccccatt gacgtcaatg ggagtttgtt ttggcaccaa aatcaacggg actttccaaa    3300
atgtcgtaac aactccgccc cattgacgca aatgggcggt aggcatgtac ggtgggaggt    3360
ctatataagc agagctcgtt tagtgaaccg tcagatcgcc tggagacgcc atccacgctg    3420
ttttgacctc catagaagac accgggaccg atccagcctc cgcggcccca agctagtcga    3480
ctttaagctt ctcgagaatt cgtgcaccat ggtgaaggta ccctggttcc caagaaaagt    3540
gtcagagctg gacaagtgtc atcacctggt caccaagttc gaccccgacc tggacttgga    3600
ccaccccggc ttctcggacc aggtgtaccg ccagcgcagg aagctgatcg ctgagatcgc    3660
cttccagtac aggcacggcg acccgatccc ccgtgtggag tacaccgccg aggagatcgc    3720
cacctggaag gaggtctaca ccaccctgaa ggggcctctac gccacccacg cctgcgggga    3780
gcacctggag gcctttgctt tgctggagcg cttcagcggc taccgggaag acaacatccc    3840
ccagctggag gacgtctccc gcttcctgaa ggagcgcaca ggcttccagc tgcggcccgt    3900
ggccggcctg ctgtccgccc gggacttcct ggccagcctg gccttccgcg tgttccagtg    3960
cacccagtat atccgccacg cgtcctcgcc catgcactcc cctgagcggg actgctgcca    4020
cgagctgctg gggcacgtgc ccatgctggc cgaccgcacc ttcgcgcagt tcagccagga    4080
catcggcctg gcgtccctgg gggccagcga tgaggaaatc gagaagctgt ccactctgta    4140
ctggttcacg gtggagttcg ggctgtgtaa gcagaacggg gaggtgaagg cctatggtgc    4200
cgggctgctg tcctcctacg gggagctcct gcactgcctg tctgaggagc ctgagatccg    4260
ggccttcgac cctgaggctg cggccgtgca gccctaccaa gaccagacgt accagtcagt    4320
ctacttcgtg tctgagagct tcagcgacgc caaggacaag ctcaggagct atgccagccg    4380
catccagcgc cccttctccg tgaagttcga cccgtacacc ctggccatcg acgtgctgga    4440
cagcccccag gccgtgcggc gctccctgga gggtgtccag gatgagctgg acacccttgc    4500
ccatgcgctg agcgccatcg gctgagcagt ggcggccgca ctagaggaat cgcccctct    4560 ccctccccc cccctaacgt tactggccga agccgcttgg aataaggccg gtgtgtgttt    4620
gtctatatgt gattttccac catattgccg tcttttggca atgtgagggc ccggaaacct    4680
ggccctgtct tcttgacgag cattcctagg ggtctttccc ctctcgccaa aggaatgcaa    4740
ggtctgttga atgtcgtgaa ggaagcagtt cctctggaag cttcttgaag acaaacaacg    4800
tctgtagcga ccctttgcag gcagcggaac cccccacctg gcgacaggtg cctctgcggc    4860
caaaagccac gtgtataaga tacacctgca aaggcggcac aaccccagtg ccacgttgtg    4920
agttggatag ttgtggaaag agtcaaatgg ctctcctcaa gcgtagtcaa caaggggctg    4980
aaggatgccc agaaggtacc ccattgtatg ggaatctgat ctggggcctc ggtgcacatg    5040
ctttacatgt gtttagtcga ggttaaaaaa gctctaggcc ccccgaacca cggggacgtg    5100
```

```
gttttccttt gaaaaacacg atgataccat ggacgccagt gagttccgaa ggcgcggcaa    5160
ggagatggtg gactacgtgg ccaactacat ggaaggcatc gagggccgcc aagtctaccc    5220
cgacgtggag cccggctacc tgcgcccgct gatccccgcc gctgcccctc aggagcccga    5280
caccttcgag gacatcatca cgacgtggga aagatcatc atgcctggcg tgacgcactg    5340
gcacagcccc tacttcttcg cctacttccc caccgccagc tcgtacccgg ccatgctggc    5400
ggacatgctg tgcggggcca ttggctgcat cggcttctcc tgggcggcga gcccagcgtg    5460
caccgagctg gagaccgtga tgatggactg gctcgggaag atgctggagc tcccaaaggc    5520
gttcttgaac gagaaggctg gcgaggggg cggcgtgatc cagggcagcg ccagcgaggc    5580
caccctggtg gccctgctgg ccgctcggac caaagtgatc caccggctgc aggcagcgtc    5640
cccagagctc acccaggccg ctatcatgga gaagctggtg gcttactcct ccgatcaggc    5700
acactcctcc gtggaacgcg ctgggctcat tggtggagtg aagctcaagg ccatccccag    5760
cgatggcaac ttcgccatgc gtgcgagcgc cctgcaggaa gccctggaga gacaaggc    5820
ggctggcctg attcctttct tcatggtggc caccctgggg accacaacat gctgctcctt    5880
cgacaacctc ctcgaagtcg gtcctatctg caacaaggaa gacatctggc tgcacgttga    5940
tgcagcctac gcaggcagcg cattcatctg ccctgagttc cggcaccttc tgaacggagt    6000
ggagttcgca gatagcttca acttcaatcc ccacaagtgg ctattggtga atttcgactg    6060
cagcgccatg tgggtgaaga gcgcaccga cctcacggga ccttccgcc tggaccccac    6120
ttacctgaag cacagccacc aggattcagg gcttatcact gactaccggc actggcagat    6180
cccactgggc cgcagattcc gcagcttgaa gatgtggttc gtattcagga tgtatggagt    6240
caagggactg caggcttata ccgcaagca tgtccagctg tcccatgagt ttgagtcact    6300
ggtgcgccag gatccccgct ttgaaatctg tgtggaagtc attctggggc ttgtctgctt    6360
tcggctaaag ggttccaaca aagtgaatga agctcttctg caaaggatca acagtgccaa    6420
aaaaatccac ttggttccat gtcacctcag ggacaagttt gtcctgcgct ttgccatctg    6480
ttctcgcacc gtggaatctg cccatgtgca gcgggcctgg aacacatca aagagctggc    6540
ggccgacgtg ctgcgagcag agagggagta gctcgaaaac ccgctgatca gcctcgactg    6600
tgccttctag ttgccagcca tctgttgttt gcccctcccc cgtgccttcc ttgagaattc    6660
ctcgacgtag atatcttaaa acagctctgg ggttgtaccc accccagagg cccacgtggc    6720
ggctagtact ccggtattgc ggtacctttg tacgcctgtt ttatactccc ttcccccgta    6780
acttagaagc acaatgtcca agttcaatag gagggggtac aaaccagtac caccacgaac    6840
aagcacttct gttcccccgg tgaggctgta taggctgttt ccacggctaa aagcggctga    6900
tccgttatcc gctcatgtac ttcgagaagc ctagtatcac cttggaatct cgatgcgtt    6960
gcgctcaaca ctcaacccca gagtgtagct taggtcgatg agtctggacg ttcctcaccg    7020
gcgacggtgg tccaggctgc gttggcggcc tacctgtggc ccaaagccac aggacgctag    7080
ttgtgaacaa ggtgtgaaga gcctattgag ctacctgaga gtcctccggc ccctgaatgc    7140
ggctaatcct aaccacggag caggcagtgg caatccagcg accagcctgt cgtaacgcgc    7200
aagttcgtgg cggaaccgac tactttgggt gtccgtgttt cctttattt ttacaatggc    7260
tgcttatggt gacaatcatt gattgttatc ataaagcaaa ttggattggc catccggtga    7320
gaatttgatt attaaattac tctcttgttg ggattgctcc tttgaaatct gtgcactca    7380
cacctattgg aattacctca ttgttaaacg cgtctagcta gcgccaccat ggagaagggc    7440
```

```
cctgtgcgcg ccccggccga gaagccgcgc ggcgcccgct gcagcaatgg gttccccgag    7500
cgcgacccgc cgcgccccgg gcccagcagg ccggccgaga agccccgcg ccccgaggcc     7560 aagagcgcgc agcccgcgga cggctggaag ggcgagcgcc cccgcagcga ggaggacaac    7620
gagctgaacc tccctaacct ggccgccgcc tactcctcca tcctgagctc gctgggcgag    7680 aaccccagc ggcaggggct gctcaagacc ccctggaggg cggcctcggc catgcagttc     7740
ttcaccaagg gctaccagga gaccatctca gacgtcctga cgacgctat cttcgacgaa    7800 gatcacgatg agatggtgat cgtgaaggac atagacatgt tctccatgtg cgagcaccac    7860
ctggtgccat ttgtgggaaa ggtccatatc ggctacctgc taacaagca ggtcctgggc     7920 ctcagcaagc tggcgaggat tgtggaaatc tatagtagaa gactacaggt tcaggagcgc    7980
cttaccaaac aaattgctgt ggcaatcacg gaagccttgc ggcctgctgg agtcggggtc    8040
gtggtggaag caacacacat gtgtatggtg atgcgaggtg tacagaaaat gaacagcaaa    8100
accgtgacca gcacaatgct gggtgtgttc cgggaggatc caaagactcg ggaagagttc    8160
ctgactctca tcaggagctg aagaattcct cgacagctta tcgataatca acctctggat    8220
tacaaaattt gtgaaagatt gactggtatt cttaactatg ttgctccttt tacgctatgt    8280
ggatacgctg cttaatgcc tttgtatcat gctattgctt cccgtatggc tttcattttc     8340
tcctccttgt ataaatcctg gttgctgtct ctttatgagg agttgtggcc cgttgtcagg    8400
caacgtggcg tggtgtgcac tgtgtttgct gacgcaaccc ccactggttg gggcattgcc    8460
accacctgtc agctccttc cgggactttc gctttccccc tccctattgc cacggcggaa    8520
ctcatcgccg cctgccttgc ccgctgctgg acagggctc ggctgttggg cactgacaat     8580
tccgtggtgt tgtcggggaa atcatcgtcc tttccttggc tgctcgcctg tgttgccacc    8640
tggattctgc gcgggacgtc cttctgctac gtcccttcgg ccctcaatcc agcggacctt    8700
ccttcccgcg gcctgctgcc ggctctgcgg cctcttccgc gtcttcgcct tcgccctcag    8760
acgagtcgga tctccctttg ggccgcctcc ccgcatcgat accgtcgaat tggaagagct    8820
ttaaatcctg gcacatctca tgtatcaatg cctcagtatg tttagaaaaa caaggggga     8880 actgtggggt tttatgagg ggttttatac aattgggcac tcagattctg cggtctgagt     8940 ccccttctctg ctgggctgaa aaggccttg taataaatat aattctctac tcagtccctg     9000
tctctagttt gtctgttcga gatcctacag agctcatgcc ttggcgtaat catggtcata    9060
gctgtttcct gtgtgaaatt gttatccgct cacaattcca cacaacatac gagccgggag    9120
cataaagtgt aaagcctggg gtgcctaatg agtgagctaa ctcacattaa ttgcgttgcg    9180
ctcactgccc gctttccagt cgggaaacct gtcgtgccag ctgcattaat gaatcggcca    9240
acgcgcgggg agaggcggtt tgcgtattgg gcgctcttcc gcttcctcgc tcactgactc    9300
gctgcgctcg tcgttcggc tgcggcgagc ggtatcagct cactcaaagg cggtaatacg     9360
gttatccaca gaatcagggg ataacgcagg aaagaacatg tgagcaaaag ccagcaaaa    9420 ggccaggaac cgtaaaaagg ccgcgttgct ggcgtttttc cataggctcc gcccccctga    9480
cgagcatcac aaaaatcgac gctcaagtca gaggtggcga aacccgacag gactataaag    9540
ataccaggcg tttccccctg gaagctccct cgtgcgctct cctgttccga ccctgccgct    9600
taccggatac ctgtccgcct ttctccctc gggaagcgtg cgctttctc atagctcacg      9660 ctgtaggtat ctcagttcgg tgtaggtcgt tcgctccaag ctgggctgtg tgcacgaacc    9720
ccccgttcag cccgaccgct gcgccttatc cggtaactat cgtcttgagt ccaacccggt    9780
aagacacgac ttatcgccac tggcagcagc cactggtaac aggattagca gagcgaggta    9840
```

-continued

```
tgtaggcggt gctacagagt tcttgaagtg gtggcctaac tacggctaca ctagaaggac    9900
agtatttggt atctgcgctc tgctgaagcc agttaccttc ggaaaaagag ttggtagctc    9960
ttgatccggc aaacaaacca ccgctggtag cggtggtttt tttgtttgca agcagcagat   10020
tacgcgcaga aaaaaggat ctcaagaaga tcctttgatc ttttctacgg ggtctgacgc    10080
tcagtggaac gaaaactcac gttaagggat tttggtcatg agattatcaa aaaggatctt   10140
cacctagatc cttttaaatt aaaaatgaag ttttaaatca atctaaagta tatatgagta   10200
aacttggtct gacagttacc aatgcttaat cagtgaggca cctatctcag cgatctgtct   10260
atttcgttca tccatagttg cctgactccc cgtcgtgtag ataactacga tacgggaggg   10320
cttaccatct ggccccagtg ctgcaatgat accgcgagac ccacgctcac cggctccaga   10380
tttatcagca ataaaccagc cagccggaag ggccgagcgc agaagtggtc ctgcaacttt   10440
atccgcctcc atccagtcta ttaattgttg ccgggaagct agagtaagta gttcgccagt   10500
taatagtttg cgcaacgttg ttgccattgc tacaggcatc gtggtgtcac gctcgtcgtt   10560
tggtatggct tcattcagct ccggttccca acgatcaagg cgagttacat gatcccccat   10620
gttgtgcaaa aaagcggtta gctccttcgg tcctccgatc gttgtcagaa gtaagttggc   10680
cgcagtgtta tcactcatgg ttatggcagc actgcataat tctcttactg tcatgccatc   10740
cgtaagatgc ttttctgtga ctggtgagta ctcaaccaag tcattctgag aatagtgtat   10800
gcggcgaccg agttgctctt gcccggcgtc aatacgggat aataccgcgc cacatagcag   10860
aactttaaaa gtgctcatca ttggaaaacg ttcttcgggg cgaaaactct caaggatctt   10920
accgctgttg agatccagtt cgatgtaacc cactcgtgca cccaactgat cttcagcatc   10980
ttttactttc accagcgttt ctgggtgagc aaaaacagga aggcaaaatg ccgcaaaaaa   11040
gggaataagg gcgacacgga aatgttgaat actcatactc ttcctttttc aatattattg   11100
aagcatttat cagggttatt gtctcatgag cggatacata tttgaatgta tttagaaaaa   11160
taaacaaata ggggttccgc gcacatttcc ccgaaaagtg ccacctaaat tgtaagcgtt   11220
aatattttgt taaaattcgc gttaaatttt tgttaaatca gctcattttt taaccaatag   11280
gccgaaatcg gcaaaatccc ttataaatca aagaataga ccgagatagg gttgagtgtt   11340
gttccagttt ggaacaagag tccactatta agaacgtgg actccaacgt caagggcga    11400 aaaaccgtct atcagggcga tggcccacta cgtgaaccat caccctaatc aagttttttg   11460
gggtcgaggt gccgtaaagc actaaatcgg aaccctaaag ggagccccg atttagagct   11520 tgacggggaa agccaacctg gcttatcgaa attaatacga ctcactatag ggagaccggc   11580
agatcttgaa aataaaatg tgtgtttgtc cgaaatacgc gt                        11622
```

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
gtgaattcgc ggccgcaatc aacctct                                          27
```

<210> SEQ ID NO 9
<211> LENGTH: 52
<212> TYPE: DNA
<213> ORGANISM: Artificial Sequence

```
-continued

<220> FEATURE:
<223> OTHER INFORMATION: Description of Artificial Sequence: Synthetic
      primer

<400> SEQUENCE: 9
ggtggcaaca caggcgagca gccccgagtc tcagcagacc ttccccgaca ac          52

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccgtggtgtt gtcggggaag gtctgctgag actcgg                            36

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gctgtcgagc ggccgcgaat tcactagtga ttctcgac                          38
```